United States Patent
Bhagat et al.

(10) Patent No.: US 12,082,935 B2
(45) Date of Patent: Sep. 10, 2024

(54) DISPOSABLE HEALTH AND VITAL SIGNS MONITORING PATCH AND MAKING OF SAME

(71) Applicant: Nypro Inc., Clinton, MA (US)

(72) Inventors: Yusuf Abu Tayeb Bhagat, Clinton, MA (US); Patrick John Verdon, Clinton, MA (US); Daniel Robert Parsons, Clinton, MA (US); Ralph Hugeneck, Clinton, MA (US); Mark Edward Sussman, Clinton, MA (US); David Donald Logan, Clinton, MA (US); Sai Guruva Reddy Avuthu, Clinton, MA (US); Girish Satish Wable, Clinton, MA (US)

(73) Assignee: Nypro Inc., Clinton, MA (US)

( * ) Notice: Subject to any disclaimer, the term of this patent is extended or adjusted under 35 U.S.C. 154(b) by 937 days.

(21) Appl. No.: 17/253,466

(22) PCT Filed: Jun. 20, 2019

(86) PCT No.: PCT/US2019/038131
§ 371 (c)(1),
(2) Date: Dec. 17, 2020

(87) PCT Pub. No.: WO2019/246340
PCT Pub. Date: Dec. 26, 2019

(65) Prior Publication Data
US 2021/0113132 A1    Apr. 22, 2021

Related U.S. Application Data

(60) Provisional application No. 62/687,589, filed on Jun. 20, 2018.

(51) Int. Cl.
| | |
|---|---|
| *A61B 5/28* | (2021.01) |
| *A61B 5/00* | (2006.01) |
| *A61B 5/11* | (2006.01) |
| *A61B 5/257* | (2021.01) |
| *A61B 5/265* | (2021.01) |

(52) U.S. Cl.
CPC .............. *A61B 5/28* (2021.01); *A61B 5/0006* (2013.01); *A61B 5/1117* (2013.01); *A61B 5/257* (2021.01);
(Continued)

(58) Field of Classification Search
CPC ........... A61B 5/28; A61B 5/265; A61B 5/257; A61B 5/0006; A61B 5/1117; A61B 5/6833; A61B 2562/0219; A61B 2562/028
See application file for complete search history.

(56) References Cited

U.S. PATENT DOCUMENTS

| | | | |
|---|---|---|---|
| 2008/0045832 A1* | 2/2008 | McGrath | A61B 5/08 600/427 |
| 2008/0082004 A1* | 4/2008 | Banet | A61B 5/6833 600/485 |

(Continued)

FOREIGN PATENT DOCUMENTS

| | | |
|---|---|---|
| JP | 2018504171 A | 2/2018 |
| KR | 101585506 B1 | 1/2016 |

(Continued)

*Primary Examiner* — Adam Z Minchella
(74) *Attorney, Agent, or Firm* — Young Basile Hanlon & MacFarlane, P.C.

(57) ABSTRACT

A disposable vital signs monitor patch includes hydrogel based conductive adhesives which contacts skin. A medical tape bonds to the skin and has printed silver-silver chloride electrodes. The hydrogel based conductive adhesives interact between the skin and the printed silver-silver chloride electrodes. A double-sided medical tape bonds to the medical tape. A printed circuit board assembly (PCBA) includes a vital signs sensor, a flexible battery, a light emitting device (LED), connects to the printed silver-silver chloride electrodes, and bonds to the double-sided medical tape. A polyethylene foam includes a cut-out for the flexible the LED. The PCBA bonds to the polyethylene foam layer. A (Continued)

plunger operates within a cut-out on the polyethylene foam layer. An acrylic adhesive transfer tape bonds to the acrylic adhesive transfer tape. The medical tape, the double-sided medical tape, the polyethylene foam, and the acrylic adhesive transfer tape bond to seal against environmental exposure.

15 Claims, 29 Drawing Sheets

(52) U.S. Cl.
CPC ............ *A61B 5/265* (2021.01); *A61B 5/6833* (2013.01); *A61B 2562/0219* (2013.01); *A61B 2562/028* (2013.01)

(56) References Cited

U.S. PATENT DOCUMENTS

| | | | |
|---|---|---|---|
| 2008/0275356 A1 | 11/2008 | Stasz et al. | |
| 2011/0152701 A1* | 6/2011 | Buxi | A61B 5/02438 600/500 |
| 2012/0088999 A1* | 4/2012 | Bishay | A61B 5/332 600/382 |
| 2013/0030259 A1* | 1/2013 | Thomsen | A61B 5/4824 600/301 |
| 2013/0158423 A1* | 6/2013 | Kapoor | A61B 5/02405 600/523 |
| 2014/0275816 A1* | 9/2014 | Sandmore | A61B 5/14551 600/323 |
| 2014/0275932 A1* | 9/2014 | Zadig | A61B 5/02438 600/386 |
| 2016/0120433 A1 | 5/2016 | Hughes et al. | |
| 2016/0324442 A1* | 11/2016 | Zdeblick | A61B 5/0537 |
| 2019/0365272 A1* | 12/2019 | Sadeghian-Motahar | A61B 5/6832 |

FOREIGN PATENT DOCUMENTS

| | | |
|---|---|---|
| KR | 10-2016-0044270 A | 4/2016 |
| WO | 2012125425 A2 | 9/2012 |
| WO | 2014165071 A1 | 10/2014 |

* cited by examiner

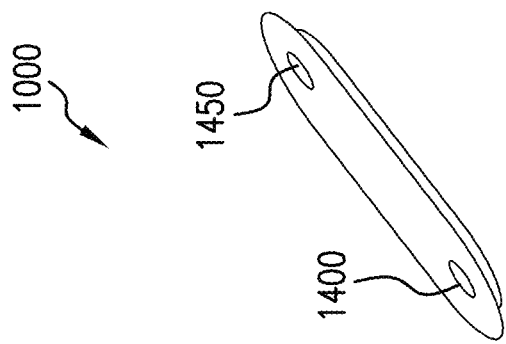
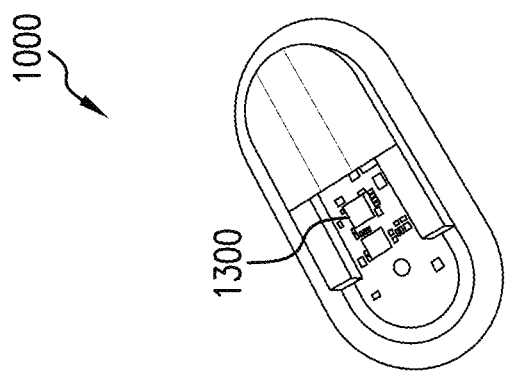
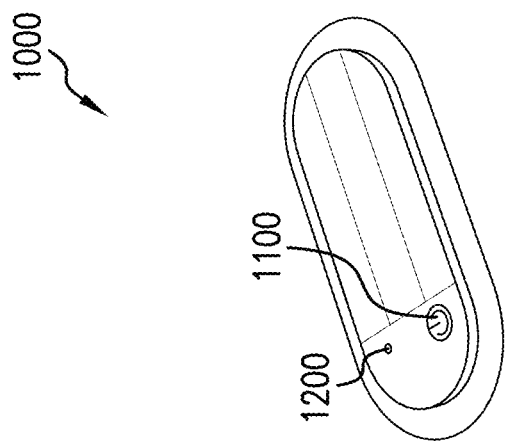

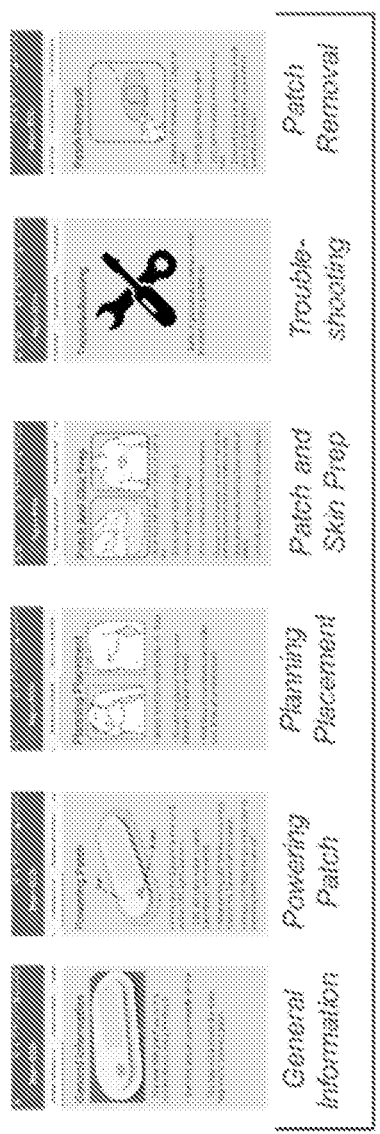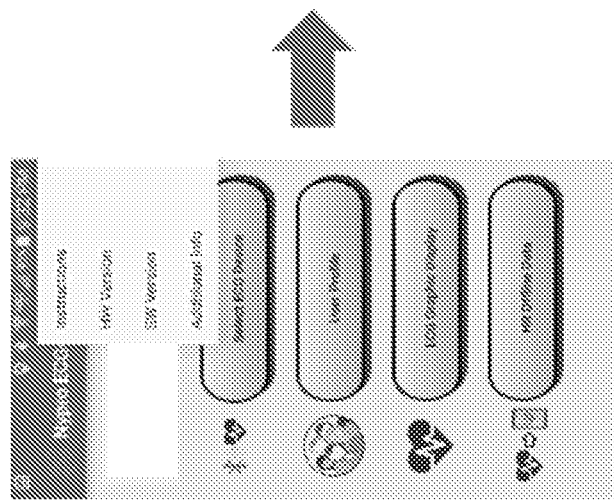
FIG. 6

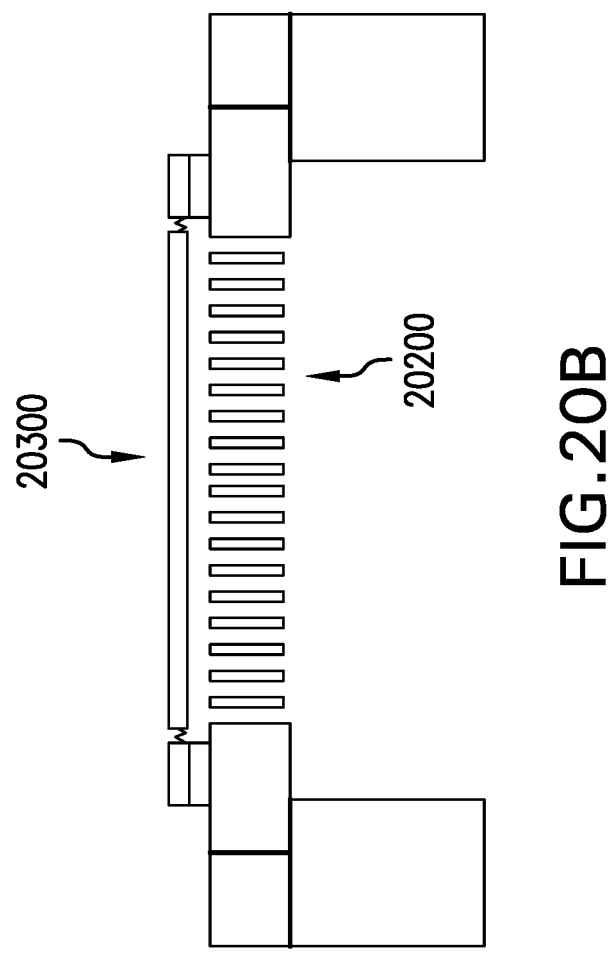

DISPOSABLE HEALTH AND VITAL SIGNS MONITORING PATCH AND MAKING OF SAME

CROSS-REFERENCE TO RELATED APPLICATION(S)

This application is a national stage 371 application of PCT/US2019/038131, filed Jun. 20, 2019, which claims priority to U.S. Provisional Application No. 62/687,589, filed Jun. 20, 2018, the entire disclosures of which are hereby incorporated by reference.

TECHNICAL FIELD

This disclosure relates to electronics and in particular, a disposable patch for monitoring health signs, vital signs, and the like.

BACKGROUND

Vital signs monitoring devices are capable of measuring multiple physiologic parameters of a patient. These physiologic parameters may include heart rate, electrocardiogram signals, and other like signals and information. The vital sign monitoring devices come in a variety of forms including smart watches, mobile phones, wearable devices, and the like. The use of such devices has become ubiquitous as users become more health conscious. The devices may be used in a variety of settings including medical facilities, home, and work, and while walking, exercising and performing other activities. The devices may be costly, need maintenance, and may be difficult to use or interpret. Consequently, there is a need for an easy to use vital signs monitoring device which may be more suitable and adaptable for a variety of environments.

SUMMARY

Disclosed herein are implementations of disposable health and/or vital signs monitoring patch and methods for making the patches or devices. A disposable vital signs monitoring patch includes multiple layers including at least two hydrogel based conductive adhesives configured to contact a user skin surface. A medical tape layer having at least a bottom surface, where the medical tape layer is configured to bond to the user skin surface, where the bottom surface includes at least two printed silver-silver chloride electrodes, and where the at least two hydrogel based conductive adhesives are configured to interact between the user skin surface and the at least two printed silver-silver chloride electrodes. A double-sided medical tape layer configured to bond to the medical tape layer. A printed circuit board assembly (PCBA) layer including at least one vital signs monitoring sensor, a flexible battery, light emitting device (LED), and is connected to the at least two printed silver-silver chloride electrodes. The PCBA is arranged to bond to the double-sided medical tape layer. A polyethylene foam layer including a cut-out for the flexible battery and the LED. The PCBA is arranged to bond to the polyethylene foam layer. A plunger arranged to operate within a cut-out on the polyethylene foam layer. An acrylic adhesive transfer tape layer having at least a bottom surface. The polyethylene foam layer is arranged to bond to the bottom surface of the acrylic adhesive transfer tape layer. The medical tape layer, the double-sided medical tape layer, the polyethylene foam layer, and the acrylic adhesive transfer tape layer are arranged and configured to provide bonding and sealing against environmental exposure. Operationally, the plunger is accessible on the acrylic adhesive transfer tape layer and configured to power on the disposable vital signs monitoring patch via the flexible battery and the light from the LED is perceivable through the acrylic adhesive transfer tape layer at defined events.

BRIEF DESCRIPTION OF THE DRAWINGS

The disclosure is best understood from the following detailed description when read in conjunction with the accompanying drawings and are incorporated into and thus constitute a part of this specification. It is emphasized that, according to common practice, the various features of the drawings are not to-scale. On the contrary, the dimensions of the various features are arbitrarily expanded or reduced for clarity.

FIGS. 1A-C are diagrams of a disposable vital signs monitoring patch in accordance with certain implementations.

FIGS. 5-12 illustrate an application that may operate with the disposable vital signs monitoring patch in accordance with certain implementations.

FIGS. 20A-B are illustrations of an illustration of a MEMS capacitive microphone as a phonocardiography sensor in a disposable vital signs monitoring patch in accordance with certain implementations.

DETAILED DESCRIPTION

Figure 2A:
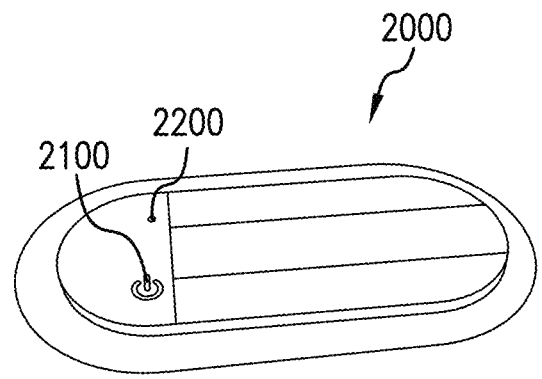
FIGS. 2A-C are photographs of a disposable vital signs monitoring patch in accordance with certain implementations.

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical similar devices, systems, compositions and methods. Those of ordinary skill may thus recognize that other elements and/or steps may be desirable or necessary to implement the devices, systems, compositions and methods described herein. However, because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art in light of the discussion herein.

Embodiments are provided throughout so that this disclosure is sufficiently thorough and fully conveys the scope of the disclosed embodiments to those who are skilled in the art. Numerous specific details are set forth, such as examples of specific aspects, devices, and methods, to provide a thorough understanding of embodiments of the present disclosure. Nevertheless, it will be apparent to those skilled in the art that certain specific disclosed details need not be employed, and that embodiments may be embodied in different forms. As such, the exemplary embodiments set forth should not be construed to limit the scope of the disclosure.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, steps, operations, elements, and/or components, but do not preclude the presence or addition of one or more other features, steps, operations, elements, components, and/or groups thereof.

The steps, processes, and operations described herein are thus not to be construed as necessarily requiring their respective performance in the particular order discussed or illustrated, unless specifically identified as a preferred or required order of performance. It is also to be understood that additional or alternative steps may be employed, in place of or in conjunction with the disclosed aspects.

Yet further, although the terms first, second, third, etc. may be used herein to describe various elements, steps or aspects, these elements, steps or aspects should not be limited by these terms. These terms may be only used to distinguish one element or aspect from another. Thus, terms such as "first," "second," and other numerical terms when used herein do not imply a sequence or order unless clearly indicated by the context. Thus, a first element, step, component, region, layer or section discussed below could be termed a second element, step, component, region, layer or section without departing from the teachings of the disclosure.

As used herein, the terminology "determine" and "identify," or any variations thereof includes selecting, ascertaining, computing, looking up, receiving, determining, establishing, obtaining, or otherwise identifying or determining in any manner whatsoever using one or more of the devices and methods are shown and described herein.

As used herein, the terminology "example," "the embodiment," "implementation," "aspect," "feature," or "element" indicates serving as an example, instance, or illustration. Unless expressly indicated, any example, embodiment, implementation, aspect, feature, or element is independent of each other example, embodiment, implementation, aspect, feature, or element and may be used in combination with any other example, embodiment, implementation, aspect, feature, or element.

As used herein, the terminology "or" is intended to mean an inclusive "or" rather than an exclusive "or." That is unless specified otherwise, or clear from context, "X includes A or B" is intended to indicate any of the natural inclusive permutations. That is if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from the context to be directed to a singular form.

As used herein, the terminology "computer" or "computing device" includes any unit, or combination of units, capable of performing any method, or any portion or portions thereof, disclosed herein. For example, the "computer" or "computing device" may include at least one or more processor(s).

As used herein, the terminology "processor" indicates one or more processors, such as one or more special purpose processors, one or more digital signal processors, one or more microprocessors, one or more controllers, one or more microcontrollers, one or more application processors, one or more central processing units (CPU)s, one or more graphics processing units (GPU)s, one or more digital signal processors (DSP)s, one or more application specific integrated circuits (ASIC)s, one or more application specific standard products, one or more field programmable gate arrays, any other type or combination of integrated circuits, one or more state machines, or any combination thereof.

As used herein, the terminology "memory" indicates any computer-usable or computer-readable medium or device that can tangibly contain, store, communicate, or transport any signal or information that may be used by or in connection with any processor. For example, a memory may be one or more read-only memories (ROM), one or more random access memories (RAM), one or more registers, low power double data rate (LPDDR) memories, one or more cache memories, one or more semiconductor memory devices, one or more magnetic media, one or more optical media, one or more magneto-optical media, or any combination thereof.

As used herein, the terminology "instructions" may include directions or expressions for performing any method, or any portion or portions thereof, disclosed herein, and may be realized in hardware, software, or any combination thereof. For example, instructions may be implemented as information, such as a computer program, stored in memory that may be executed by a processor to perform any of the respective methods, algorithms, aspects, or combinations thereof, as described herein. Instructions, or a portion thereof, may be implemented as a special purpose processor, or circuitry, that may include specialized hardware for carrying out any of the methods, algorithms, aspects, or combinations thereof, as described herein. In some implementations, portions of the instructions may be distributed across multiple processors on a single device, on multiple devices, which may communicate directly or across a network such as a local area network, a wide area network, the Internet, or a combination thereof.

As used herein, the term "application" refers generally to a unit of executable software that implements or performs one or more functions, tasks or activities. For example, applications may perform one or more functions including, but not limited to, vital signs monitoring, health monitoring, telephony, web browsers, e-commerce transactions, media players, travel scheduling and management, smart home management, entertainment, and the like. The unit of executable software generally runs in a predetermined environment and/or a processor.

The non-limiting embodiments described herein are with respect to patches or devices and methods for making the patches or devices, where the patches or devices are vital signs monitoring or health signs monitoring patches or devices. The patch or device and method for making the patch or device may be modified for a variety of applications and uses while remaining within the spirit and scope of the claims. The embodiments and variations described herein, and/or shown in the drawings, are presented by way of example only and are not limiting as to the scope and spirit. The descriptions herein may be applicable to all embodiments of the device and the methods for making the devices.

Disclosed herein are implementations of disposable health or vital (collectively "vital") signs monitoring patches or devices (collectively "patches") and methods for making the patches. The disposable vital signs monitoring patch is a disposable, external on-body, skin-contact patch. The patch is easily attached and removed from the user. The patch may use a combination of sensors, printed electronics, adhesives, batteries, and flexible materials or enclosures. The disposability aspect means that internal electronics and power supply are sealed from external exposure. This disposability aspect of the patch permits sealing of the structure to provide a dust tight patch. In addition, the patch provides protection against temporary immersion in water. In an implementation, the patch may have an International Electrotechnical Commission (IEC) protection rating of IPX 67. Due its disposability, the patch may have a small form factor including both size and weight. For example, the patch may be approximately two (2) inches by four (4) inches and may weigh 8.5 grams. This makes it easy for the user to wear without much discomfort.

In an implementation, the variety of sensors may include a single lead electrocardiogram (ECG) sensor and an accelerometer. In an implementation, the patch may include a sensor to measure phonocardiograms. In an implementation, a phonocardiogram sensor may be silver polyvinylidene difluoride (PVDF) sensors, piezoelectric sensors, poly(3,4-ethylenedioxythiophene) polystyrene sulfonate sensors, microelectromechanical systems (MEMS) microphones, MEMS piezoelectric microphones, MEMS capacitive microphones, accelerometers, and the like.

Power for the patch is internally supplied by a sealed in, flexible battery as described herein. The flexible battery may permit the patch to be run in a continuous mode of operation for a defined time period. For example, the defined time period may be 7 days. The data from the patch may be communicated to a mobile device for display or analysis. In an implementation, the communication may be done via wireless, Bluetooth®, and the like. The data may include ECG live data, heart rate, heart rate variability, fall detection, and the like.

FIGS. 1A-C are diagrams of a disposable vital signs monitoring patch 1000 in accordance with certain implementations. FIG. 1A is a top view of the disposable vital signs monitoring patch 1000 which shows a power button 1100 and a light emitting device (LED) 1200. FIG. 1B is a top cut-away view of the disposable vital signs monitoring patch 1000 which shows electronics 1300. FIG. 1C is a bottom view of the disposable vital signs monitoring patch 1000 which shows electrodes 1400 and 1450 for contacting a user skin.

Operationally, a user may activate the disposable vital signs monitoring patch 1000 using the power button 1100. In an implementation, the power button 1100 is a push button on/off switch. The LED 1200 may be used as a multifunctional indicator. The LED 1200 may blink once every 5 seconds, for example, after the power button 1100 is pressed on. The LED 1200 may blink 4 times every 2 seconds, for example, when pairing for Bluetooth® wireless communications with a device. For example, the LED 1200 may blink once every 500 milliseconds for a time interval of 2 seconds. After pairing is complete, the LED 1200 may revert back to blinking every 5 seconds for normal operation. The LED 1200 may remain on (i.e., the LED is emitting) for 2 seconds when a fall is detected. After fall detection notification, the LED 1200 may revert back to blinking every 5 seconds for normal operation. The LED 1200 may blink 2 times in succession at a frequency of 10 seconds, for example, when power level is at 20%, for example. The lack of LED emittance or signals may indicate that the disposable vital signs monitoring patch 1000 is off. Confirmation that the disposable vital signs monitoring patch 1000 is off may be done by checking whether a Bluetooth® MAC address appears for a given disposable vital signs monitoring patch 1000. Absence of the Bluetooth® MAC address confirms that the disposable vital signs monitoring patch 1000 is off. The number of blinks and time periods are illustrative and other values may be used without departing from the scope of the claims and the description.

Figure 2B:
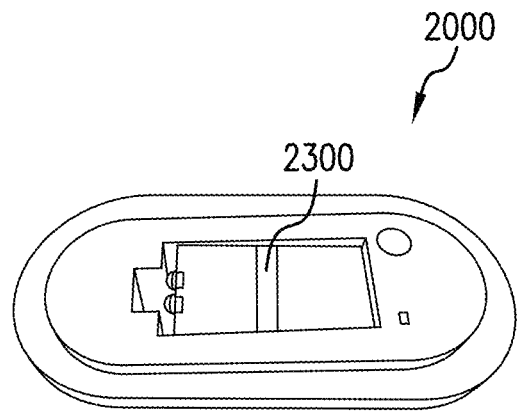
Figure 2C:
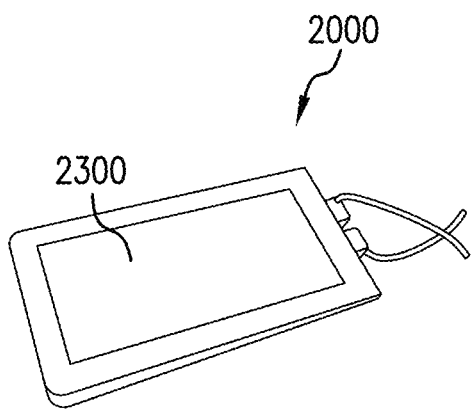

FIGS. 2A-C are photographs of a disposable vital signs monitoring patch 2000 in accordance with certain implementations. FIG. 2A is a top view of the disposable vital signs monitoring patch 2000 which shows a power button 2100 and a light emitting device (LED) 2200. FIG. 2B is a top cut-away view of the disposable vital signs monitoring patch 2000 which shows a flexible battery 2300. FIG. 2C is a view of the flexible battery 2300. In an implementation, the flexible battery 2300 is a non-rechargeable battery. In an implementation, the flexible battery 2300 is sealed with the disposable vital signs monitoring patch 2000. In an implementation, the flexible battery 2300 may be a Lithium Polymer battery. In an implementation, the flexible battery 2300 may be a stack of four Lithium Polymer batteries in a parallel configuration which may generate 3V and 140 mAh, for example.

Operationally, the disposable vital signs monitoring patch 2000 operates as described with respect to the disposable vital signs monitoring patch 1000 of FIGS. 1A-1C. In addition, the flexible battery 2300 may provide the power for the disposable vital signs monitoring patch 2000 or the disposable vital signs monitoring patch 1000.

Figure 3A:
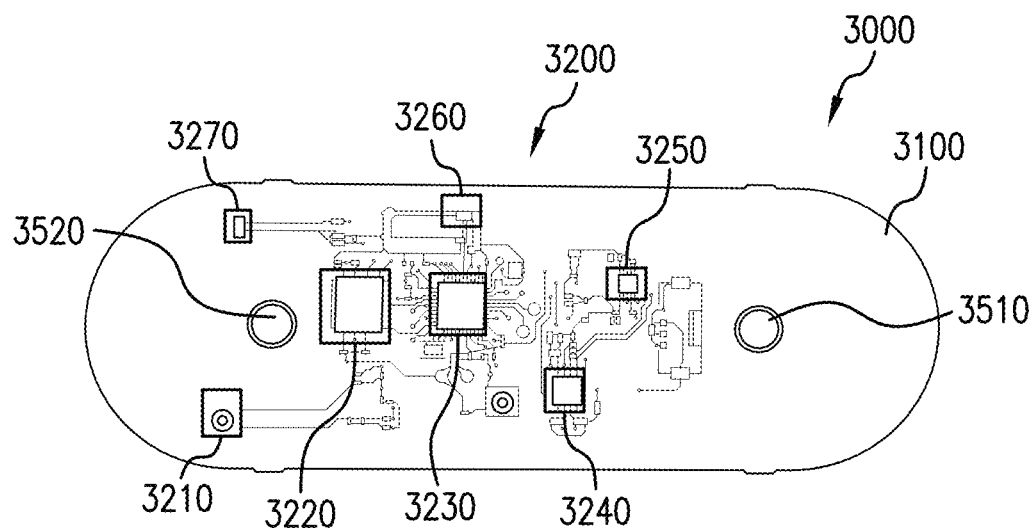
FIG. 3A-B are diagrams of a printed circuit board of a disposable vital signs monitoring patch in accordance with certain implementations.
Figure 3B:
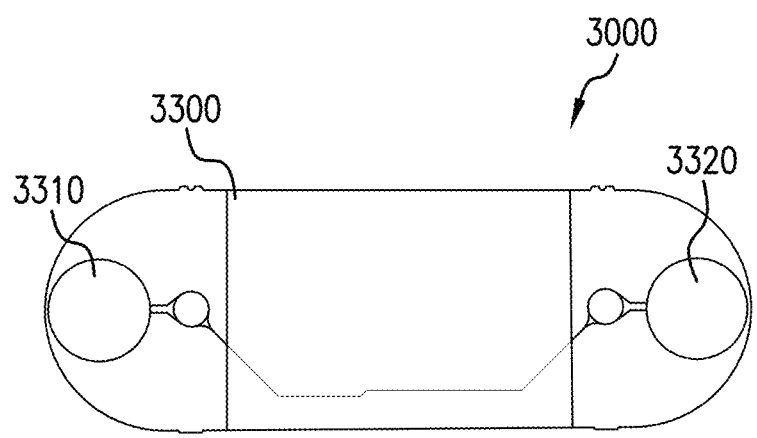

FIGS. 3A-B are photographs of a printed circuit board assembly (PCBA) 3000 of a disposable vital signs monitoring patch in accordance with certain implementations. FIG. 3A is a top surface 3100 (relative to side facing user skin) of the PCBA 3000. The top surface 3100 includes electronics 3200 which includes, for example, an on/off switch 3210, memory/storage 3220, wireless microcontroller and Bluetooth® module 3230, an ECG analog frontend 3240, an accelerometer 3250, Bluetooth® antenna 3260, and a LED 3270. The PCBA 3000 is illustrative and may include additional, fewer or different electronic components and the like which may be similarly or differently architected without departing from the scope of the specification and claims herein. Moreover, the illustrated electronic components may perform other or additional functions without departing from the scope of the specification and claims herein. FIG. 3B is a bottom surface 3300 (relative to side facing user skin) of the PCBA 3000. The bottom surface 3300 may include printed silver-silver chloride electrodes 3310 and 3320 which are connected to the electronics 3200 on the top surface 3100 of the PCBA 3000 through a three layer stack as described herein. In an implementation, non-printed electrodes may be connected to the electronics 3200 on the top surface 3100 of the PCBA 3000 via through holes 3510 and 3520.

Operationally, the electronics 3200 collectively control the functionality of the disposable vital signs monitoring patch as further described herein. For example, the on/off switch 3210 may be connected to the power button 2100 and to the flexible battery 2300 so that power may be provided to the disposable vital signs monitoring patch. The memory/storage 3220 may be used to store the data generated by the ECG sensor, accelerometer, and other sensors in the disposable vital signs monitoring patch. The ECG analog frontend 3240 may collect and display biopotential signals. The accelerometer 3250 may collect data related to inclination and fall detection. The wireless microcontroller and Bluetooth® module 3230 and the Bluetooth® antenna 3260 may permit the disposable vital signs monitoring patch to transmit data collected by the disposable vital signs monitoring patch to a device, such as a mobile device which may have a corresponding or associated application to analyze and display the collected data as described herein below.

Figure 4:
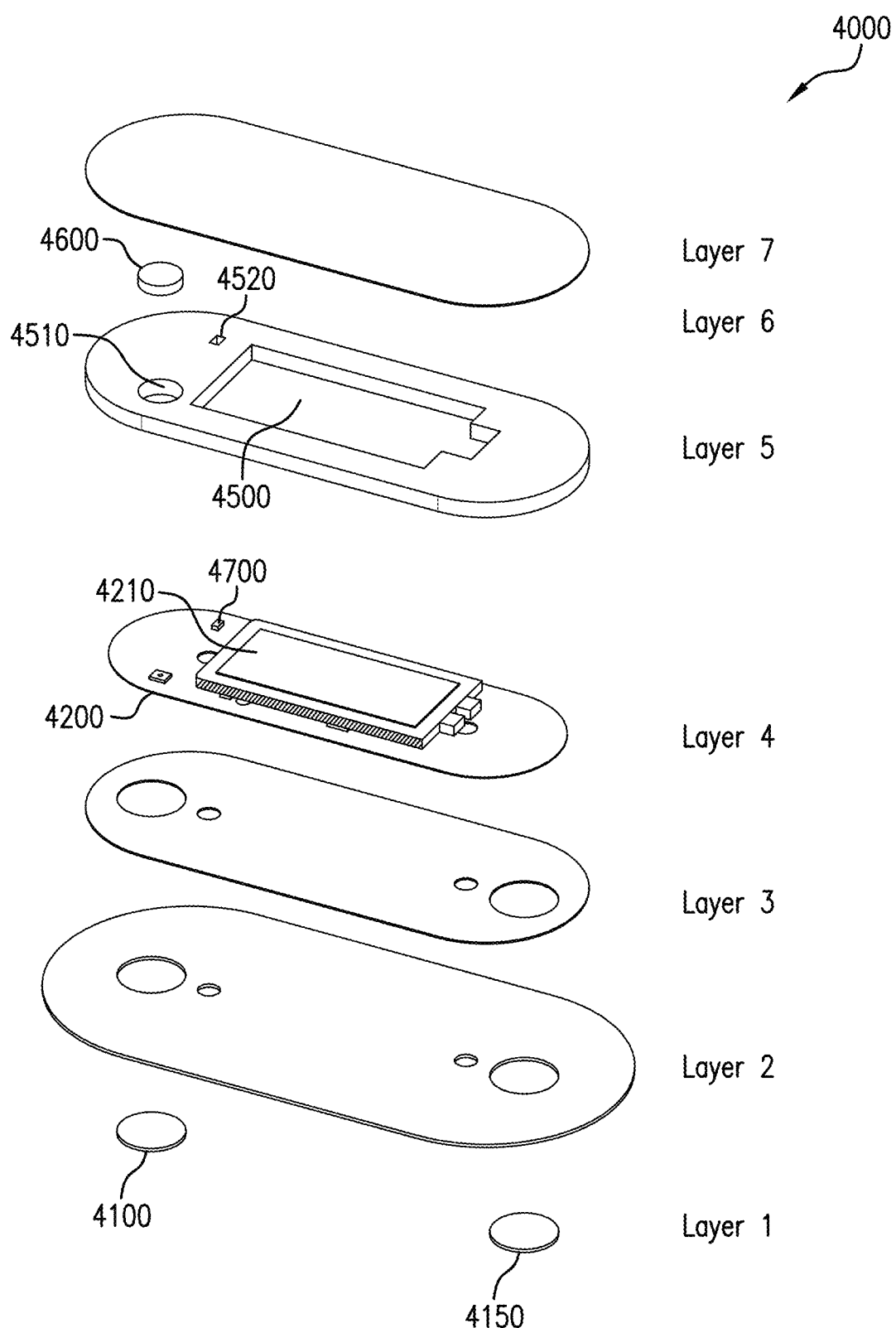
FIG. 4 is a diagram of the multiple layers in a disposable vital signs monitoring patch in accordance with certain implementations.

FIG. 4 is a diagram of the multiple layers in a disposable vital signs monitoring patch 4000 in accordance with certain implementations. Layer 1 of the disposable vital signs monitoring patch 4000 are hydrogel based conductive adhesives 4100 and 4150 which may perform as an interface between the printed silver-silver chloride electrodes and a user skin surface. Layer 2 may be a medical tape which consists of a porous, highly breathable, white elastic multi-layer polyurethane/synthetic rubber based non-woven fabric. The non-woven fabric may be coated on one side with a pressure sensitive adhesive which bonds to a user skin surface. Layer 3 is a double-sided medical tape layer which consists of a synthetic rubber adhesive on one side of the tape that adheres to Layer 2 and to the PCBA (Layer 4) on the other side. Layer 4 is a PCBA 4200 which may include a flexible battery 4210. Layer 5 is a polyethylene foam layer which may adhere to the top of Layer 4 (i.e., the PCBA 4200). The polyethylene foam layer may have a laser cut-out 4500 for encompassing the flexible battery 4210, a cut-out 4510 for a plunger 4600 (Layer 6), and a cutout 4520 for a LED light 4700 on the PCBA 4200. Layer 6 is the plunger 4600 (also shown or described as power button). The plunger 4600 is a 3D printed double side adhesive plastic piece. The plunger 4600 may actuate the on/off switch on the PCBA 4200 for turning on/off the disposable vital signs monitoring patch. Layer 7 is an acrylic adhesive transfer tape layer that bonds to Layer 5. The top surface of Layer 7 may contain design logos and the like. As noted herein, the disposable vital signs monitoring patch 4000 may meet an IPX 67 rating. This is enabled as layers 2, 3, 5 and 7 include various pressure sensitive adhesives, synthetic rubber adhesives and transfer tapes which create extremely strong bonds rendering the fully mechanically assembled device impenetrable and well-sealed against environmental exposure.

As noted herein, the disposable vital signs monitoring patch 4000 is a closed device which does not provide access to internal components such as the flexible battery 4210, the PCBA 4200, and the like. However, the disposable vital signs monitoring patch 4000 maintains flexibility in use. This was confirmed by conducting structural simulations for the disposable vital signs monitoring patch. The simulations determined if various bend angles would result in stress or strain (displacement) effects which would compromise the electronic components and flexible battery on the PCBA of the disposable vital signs monitoring patch. In the simulations, loading for each simulation was defined as an angular displacement of the ends of the patch. For each bend angle employed, values were determined for displacement and equivalent stress. For the bend angles employed (6.3°, 15.7° and 33.2°), the displacement values ranged from 0 to 16 mm and the equivalent stress values ranged from 0 to 1.6 MPa. At a bend angle of 6.3°, the displacement was moderate and observable at the periphery of Layer 2. However, the electronics were not compromised. At a bend angle of 6.3°, the stress was moderate and observable at the periphery of Layer 2. However, the electronics were not compromised. At a bend angle of 15.7°, a displacement of ~6 mm was observed at the edge of Layer 2. However, the electronics were not compromised. At a bend angle of 15.7°, the stress was moderate (~0.5-0.8 MPa) and observable at the periphery of Layers 2-5. However, the PCBA components were not compromised. At a bend angle of 33.2°, a displacement of ~16 mm was observed at the edge of Layer 2 with moderate displacement levels propagating through to Layers 4 and 5. However, the PCBA components including the flexible battery were not compromised. At a bend angle of 33.2°, a maximum stress level of 1.6 MPa was confined to the medial aspects of Layer 2 but did not propagate to Layers 4 and 5. Consequently, the PCBA components would not fail.

The disposable vital signs monitoring patch may also include an application which may run on a device such as mobile devices, end user devices, cellular telephones, Internet Protocol (IP) devices, mobile computers, laptops, handheld computers, PDAs, personal media devices, smartphones, notebooks, notepads, phablets, smart watches, and the like (collectively "user device"). The disposable vital signs monitoring patch may wirelessly communicate with the user device and the application together with the user device may analyze, display and provide alerts to a user the vitals signs data collected by the disposable vital signs monitoring patch.

Figure 5:
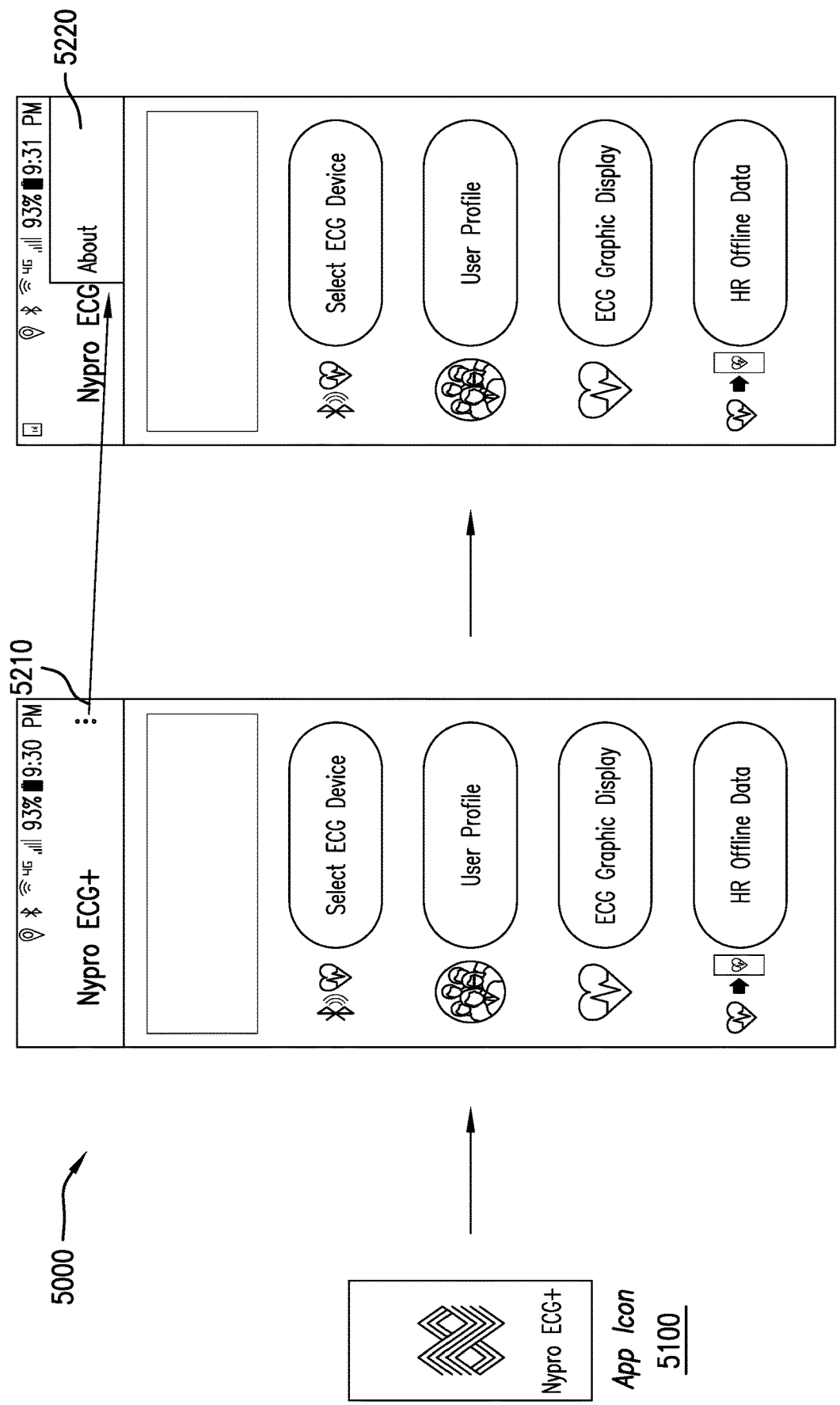
Figure 7:
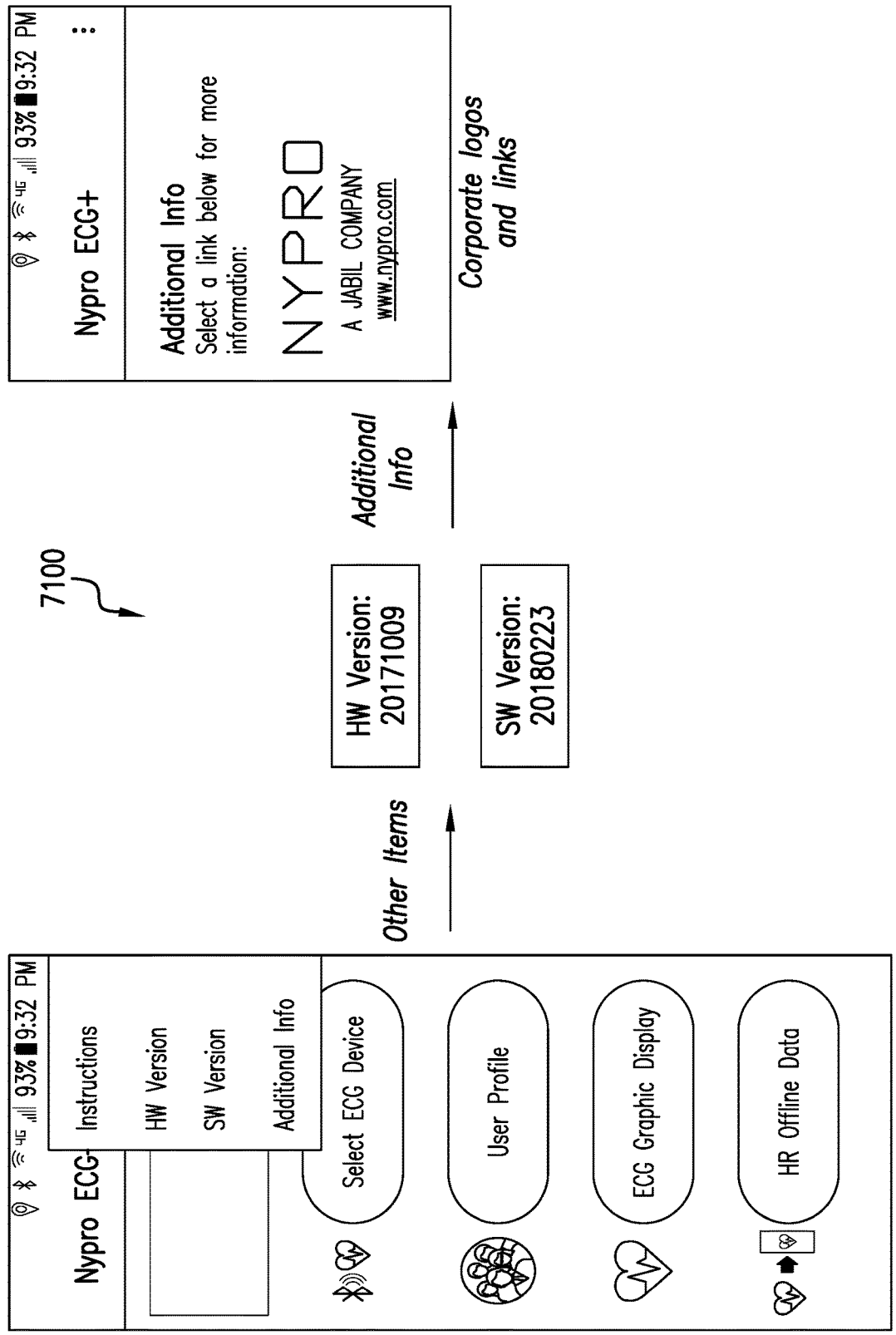

FIGS. 5-12 illustrate various aspects of the application 5000. FIG. 5 illustrates an App Icon 5100, which when clicked on opens the Main Menu page 5200. The Main Menu page 5200 includes ellipses 5210, which include an About link 5220. FIGS. 6 and 7 illustrate the contents 6100 and 7100 of the About page of the application 5000.

Figure 8:
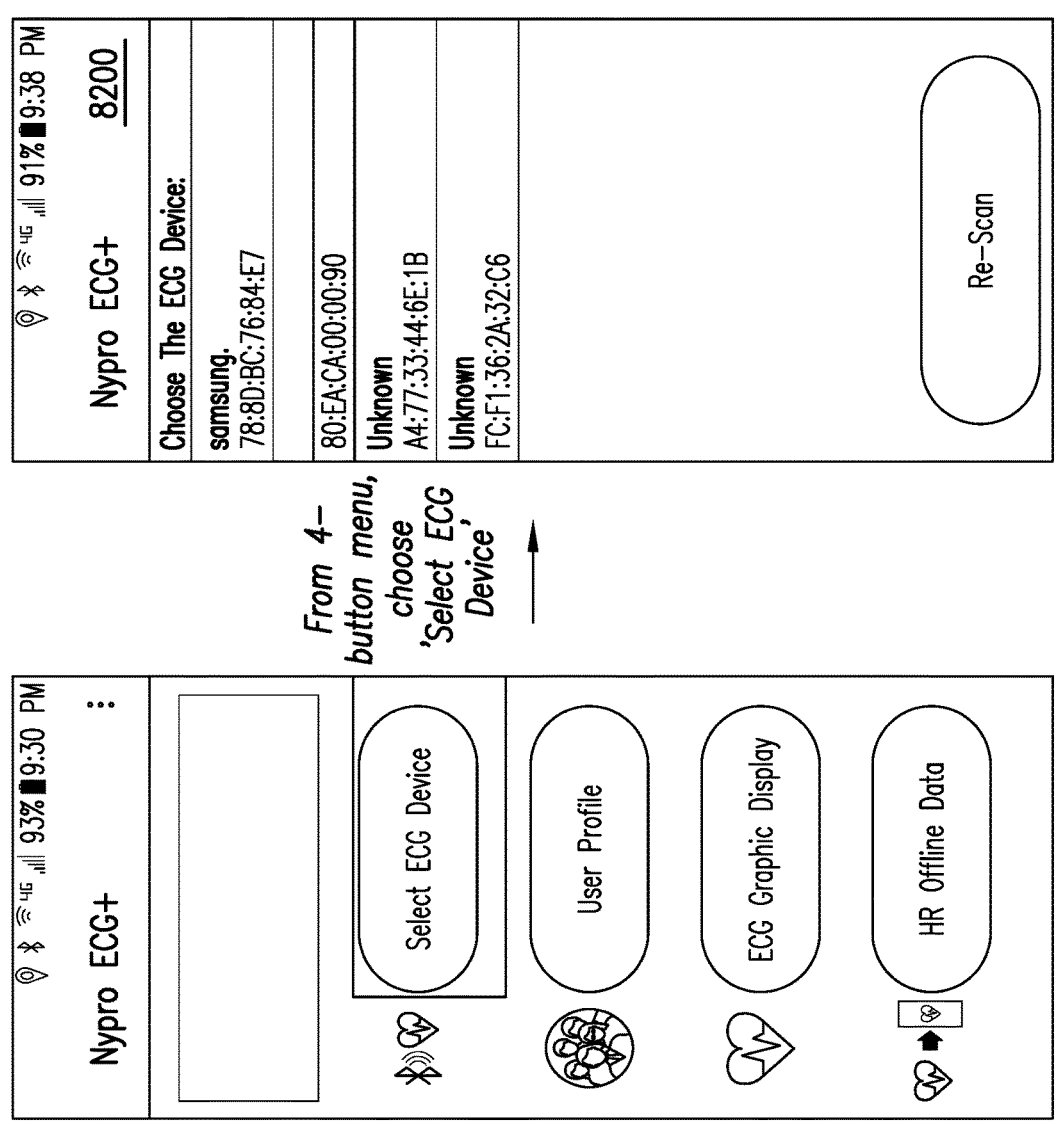
Figure 9:
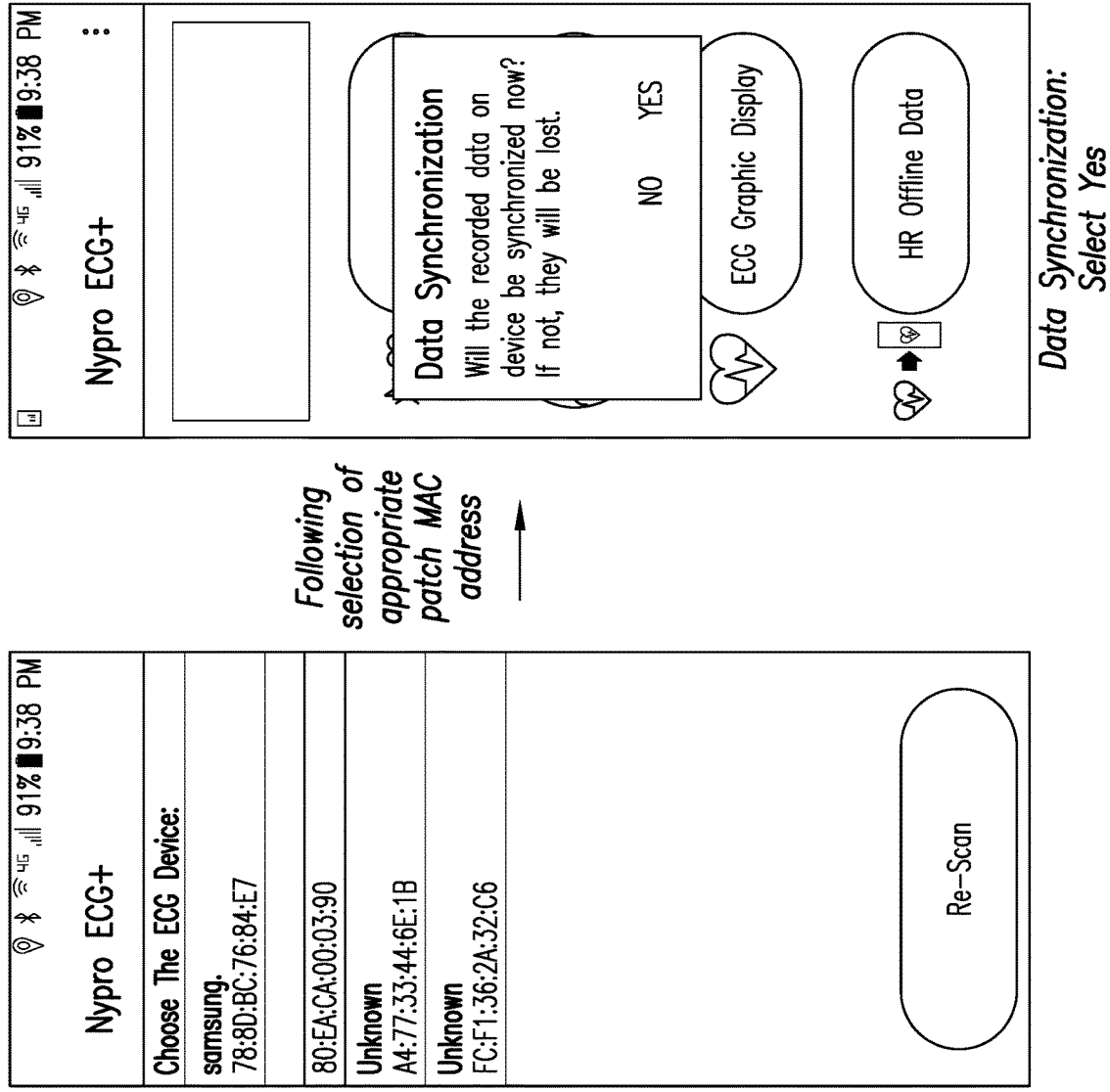
Figure 10:
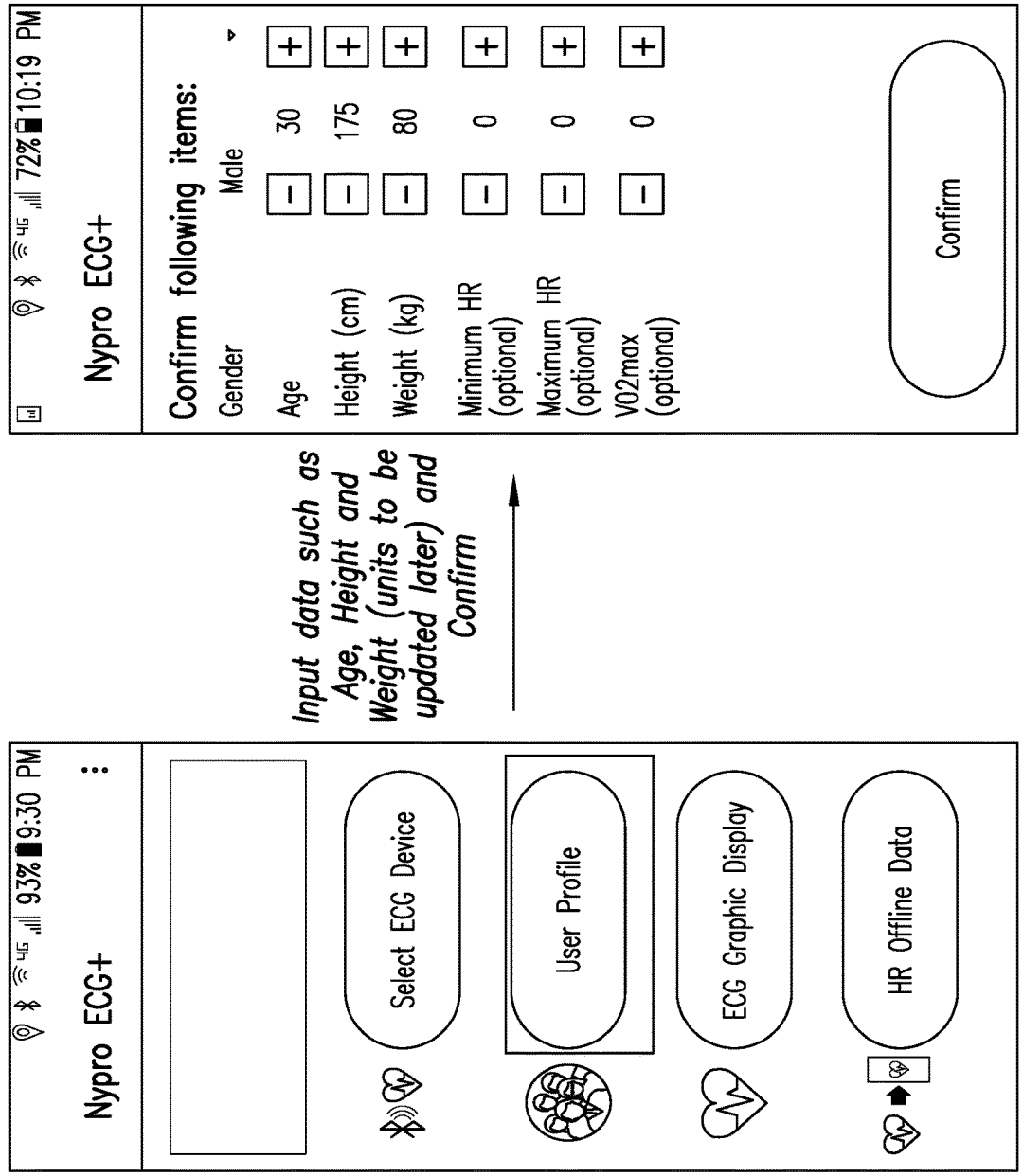

FIGS. 8-9 illustrate pairing 8100 the disposable vital signs monitoring patch with the user device as seen on the application 5000. Operationally, from the Main Menu page 5200, the button associated with Select ECG Device is clicked, which in turn shows a list 8200 of disposable vital signs monitoring patches that may be available for pairing. In an implementation, a Bluetooth® MAC address may be selected which corresponds to the barcode of the desired disposable vital signs monitoring patch. FIG. 9 illustrates an option for selecting data synchronization during the pairing process. FIG. 10 illustrates inputting of user data.

Figure 11:
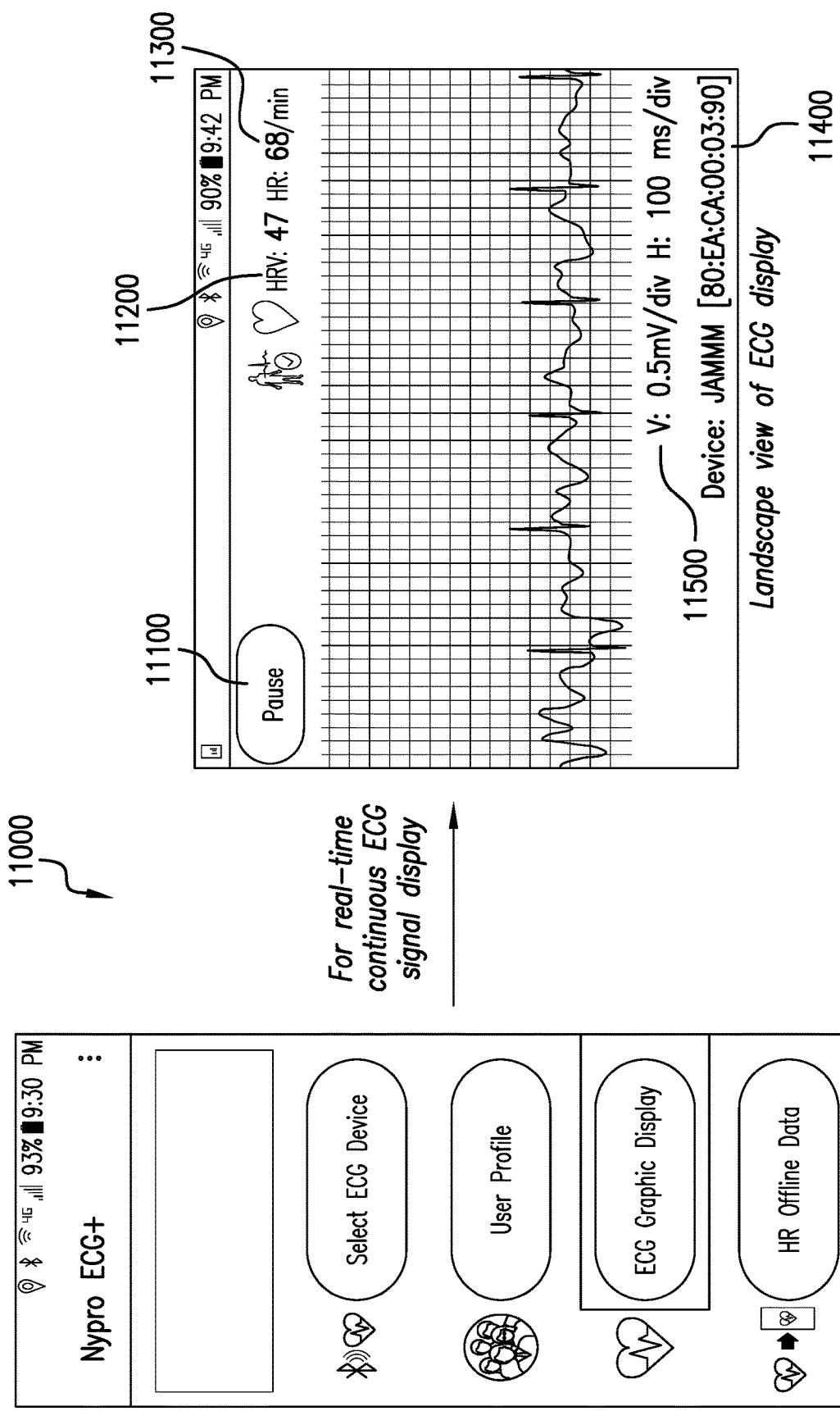
Figure 12:
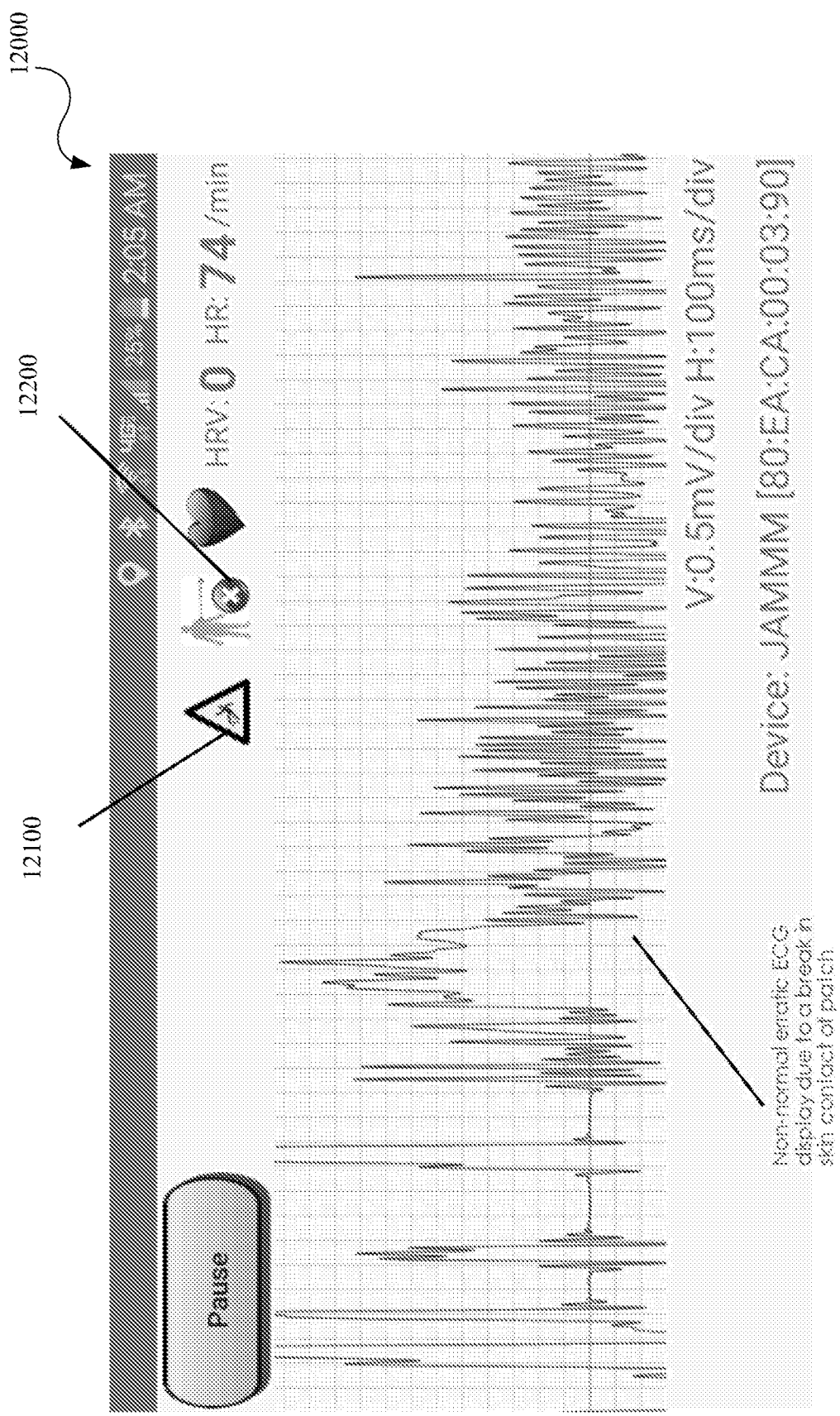

FIGS. 11-12 illustrate ECG graphical display 11000 of the data collected by the disposable vital signs monitoring patch. The ECG graphical display 11000 may show real-time continuous ECG signal display. In an implementation, the real-time continuous ECG signal display may be paused using Pause button 11100. In an implementation, the ECG graphical display 11000 may show heart rate variability 11200, heart rate 11300, the Bluetooth® MAC address 11400 for the disposable vital signs monitoring patch from which data is being obtained, and axis parameters 11500. FIG. 12 shows another view of an ECG graphical display 12000. This ECG graphical display 12000 illustrates depiction of a fall detection symbol 12100 if a fall has been detected along with an audible alert. The ECG graphical display 12000 also illustrates an icon 12200 when lack of proper skin contact or intermittent contact results to indicate insufficient signal. An illustration of non-normal erratic ECG display 12300 due to a break in skin contact of patch.

As noted, the application 5000 in concert with the user device displays the data collected from the disposable vital signs monitoring patch. This data may be streamed as a text file or like file, saved, and processed offline as needed.

The disposable vital signs monitoring patch may also include a phonocardiography sensor which may capture sounds and murmurs produced by heart, i.e., valves and vessels (auscultation areas). These may relate to mechanical events such as valvular vibrations, muscular vibrations of myocardium, vascular vibration from sudden distension of arterial walls, vibrations related to acceleration/deceleration of blood flow, and the like.

In an implementation, the phonocardiography sensor may be implemented by re-using or re-purposing the accelerometer in the vital signs monitoring patch, such as the accelerometer 3250, to detect phonocardiographic signals by registering vibrations from the opening and closing of the heart valves. The vibrational frequencies may then to correlated to specific sound frequencies.

Figure 13:
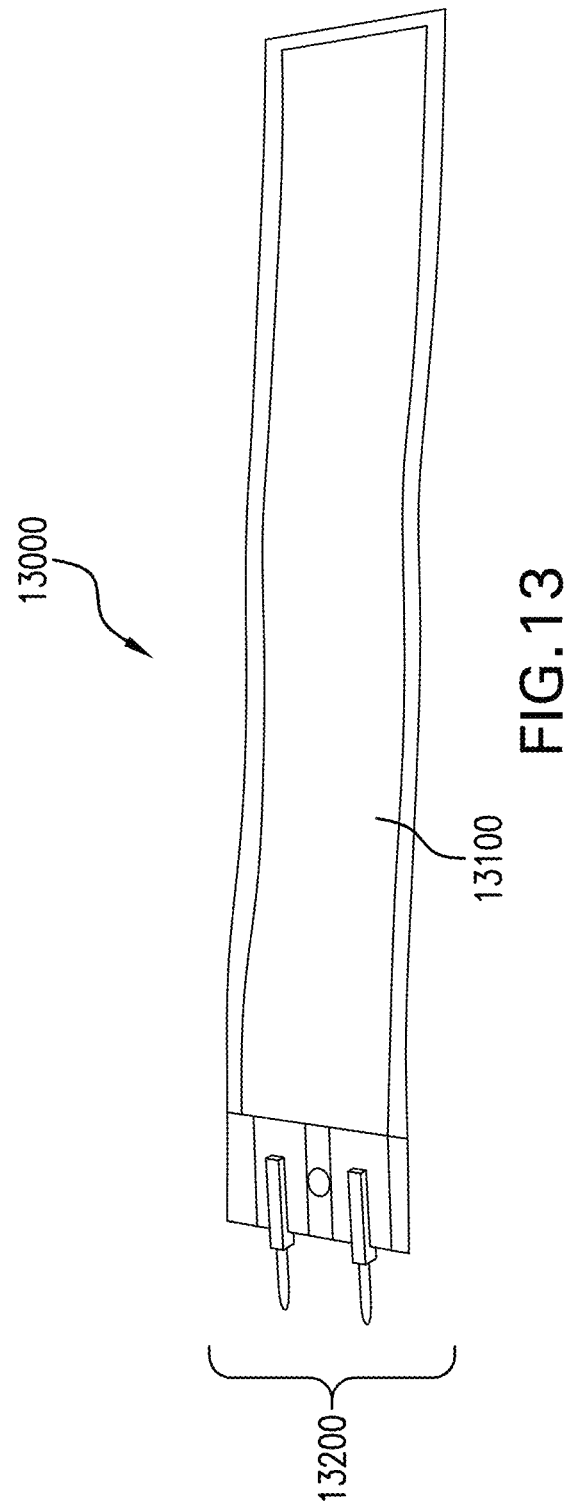
FIG. 13 is a photograph of a silver-Polyvinylidene fluoride or polyvinylidene difluoride (Ag-PVDF) piezoelectric sensor which may be used as a pressure transducer to capture and/or measure phonocardiography signals in accordance with certain implementations.
Figure 14A:
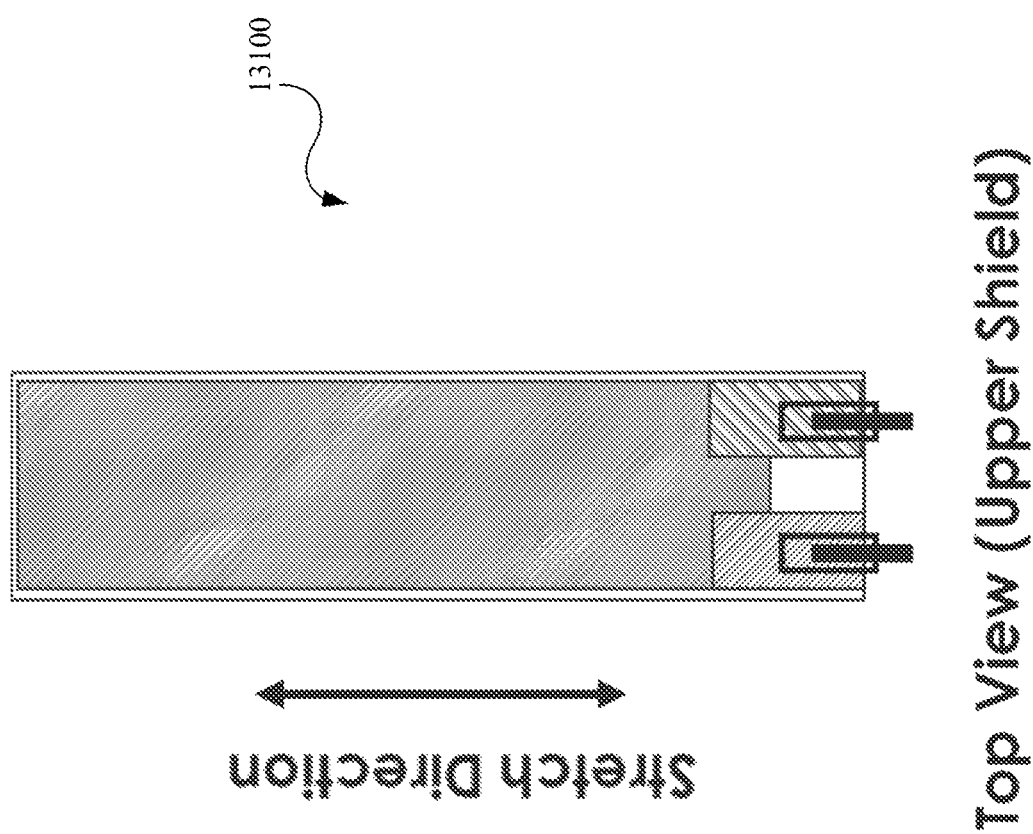
FIG. 14A is a diagram of a top view of the Ag-PVDF piezoelectric sensor of FIG. 13 in accordance with certain implementations.
Figure 14B:
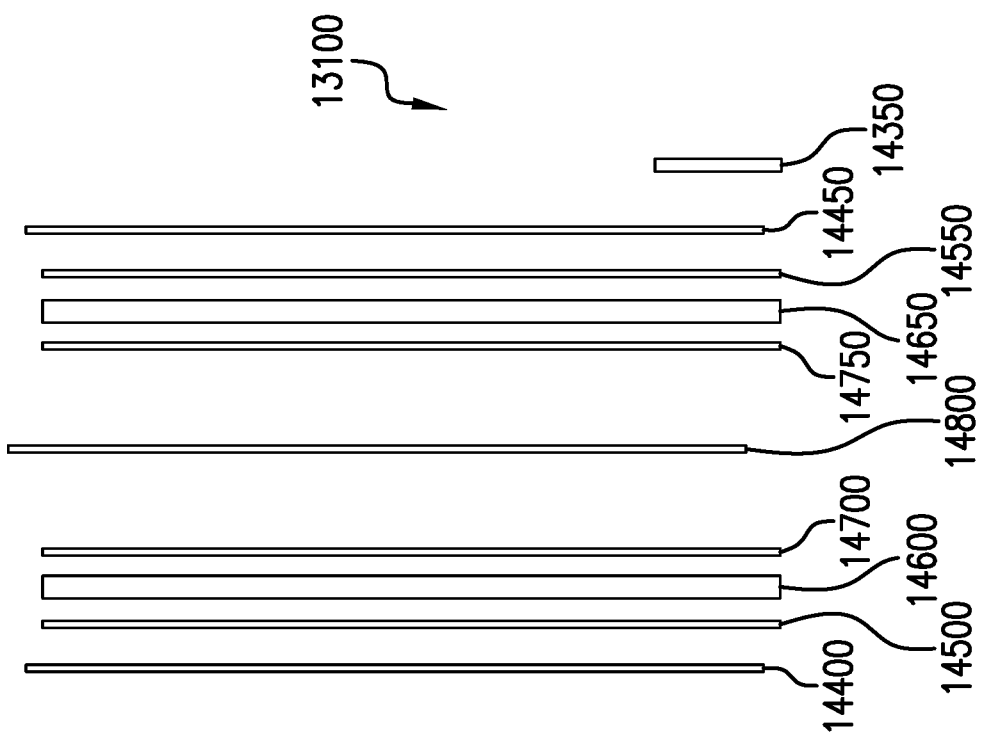
FIG. 14B is a diagram of a cross-sectional view of the Ag-PVDF piezoelectric sensor of FIG. 13 in accordance with certain implementations.
Figure 14C:
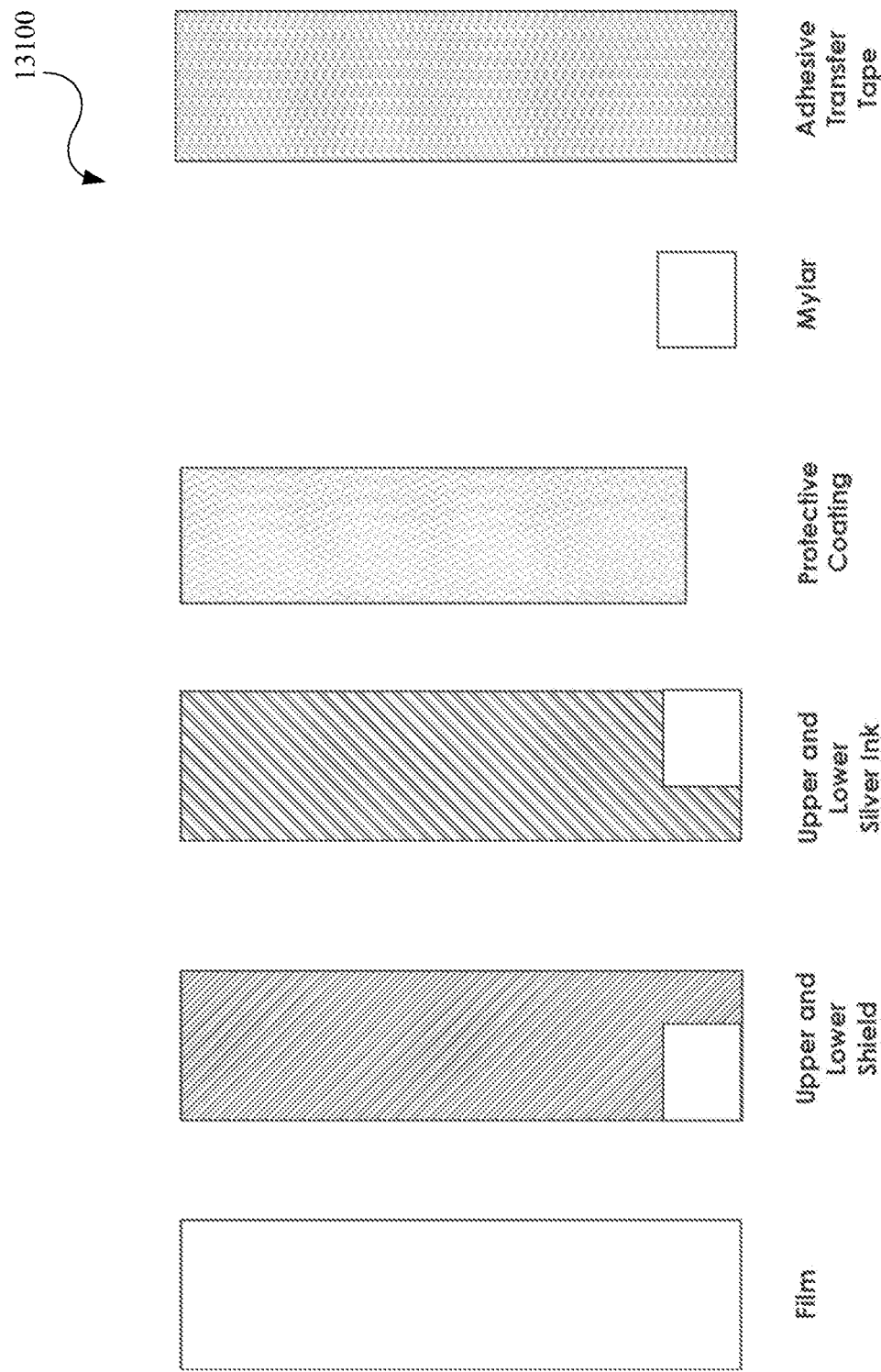
FIG. 14C is a diagram of the layers in the Ag-PVDF piezoelectric sensor of FIG. 13 in accordance with certain implementations.

In an implementation, pressure transducers may be used for capturing and/or measuring phonocardiography signals. FIGS. 13-14A-14C illustrate and describes an example pressure transducer. FIG. 13 is a photograph of a silver-Polyvinylidene fluoride or polyvinylidene difluoride (Ag-PVDF) piezoelectric sensor 13000 which may be used as a pressure transducer to capture and/or measure phonocardiography signals. The Ag-PVDF piezoelectric sensor 13000 may include a Ag-PVDF strip 13100 connected to positive and negative electrodes 13200. The Ag-PVDF piezoelectric sensor 13000 may be implemented on a skin facing side of the vital signs monitoring patch. FIG. 14A is a diagram of a top view of the Ag-PVDF piezoelectric sensor 13000 of FIG. 13. FIG. 14A shows example of the Ag-PVDF sensor strip 13100 along with its stretch direction indicating the direction of manifestation of the piezoelectric effect upon mechanical perturbation. FIG. 14B is a diagram of a cross-sectional view of the Ag-PVDF piezoelectric sensor 13000. In particular, FIG. 14B provides an exploded diagram of the various layers in a stack-up including, for example, mylar layer 14350, protective coating layers 14400 and 14450, upper and lower shield layers 14500 and 14550, film layers 14600 and 14650, upper and lower silver ink layers 14700 and 14750, and an adhesive transfer tape layer 14800. The adhesive transfer tape layer 14800 may secure the upper and lower stacks, the upper and lower silver ink layers 14700 and 14750 may serve as conductors, the film layers 14600 and 14650 are composed of a PVDF and may act as a dielectric layer, the upper and lower shield layers 14500 and 14550 are made of silver and may act as conductors, the protective coating layers 14400 and 14450 may serve as another set of dielectric layers and the mylar layer 14350 may provide contact support. FIG. 14C is a diagram of the layers in the Ag-PVDF piezoelectric sensor 13000. In particular, FIG. 14C provides an example of the various layers of the Silver-PVDF sensor strip 13100 shown in the exploded view in FIG. 14B.

Operationally, the Ag-PVDF sensor strip 14000 may stretch or deform in response to pressure changes from valvular vibrations, muscular vibrations of myocardium, vascular vibration from sudden distension of arterial walls, vibrations related to acceleration/deceleration of blood flow, and the like, and which are captured as electrical signals via the positive and negative electrodes 13200.

Figure 15:
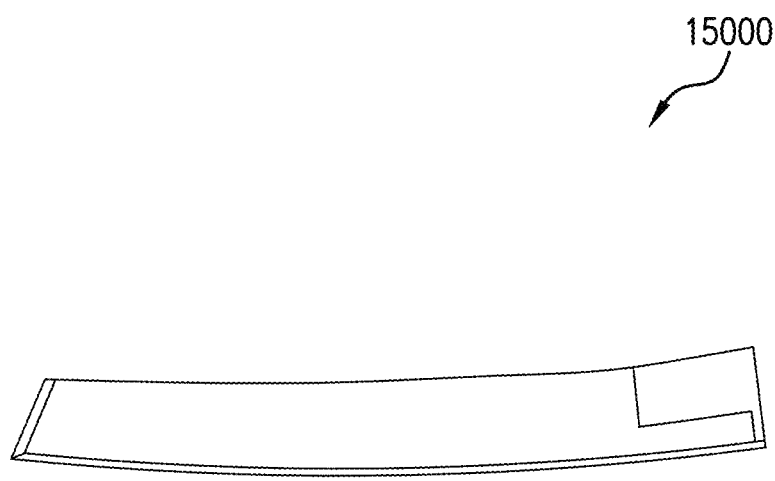
FIG. 15 is a photograph of a poly(3,4-ethylenedioxythiophene) polystyrene sulfonate piezoelectric sensor which may be used as a pressure transducer to capture and/or measure phonocardiography signals in accordance with certain implementations.
Figure 16:
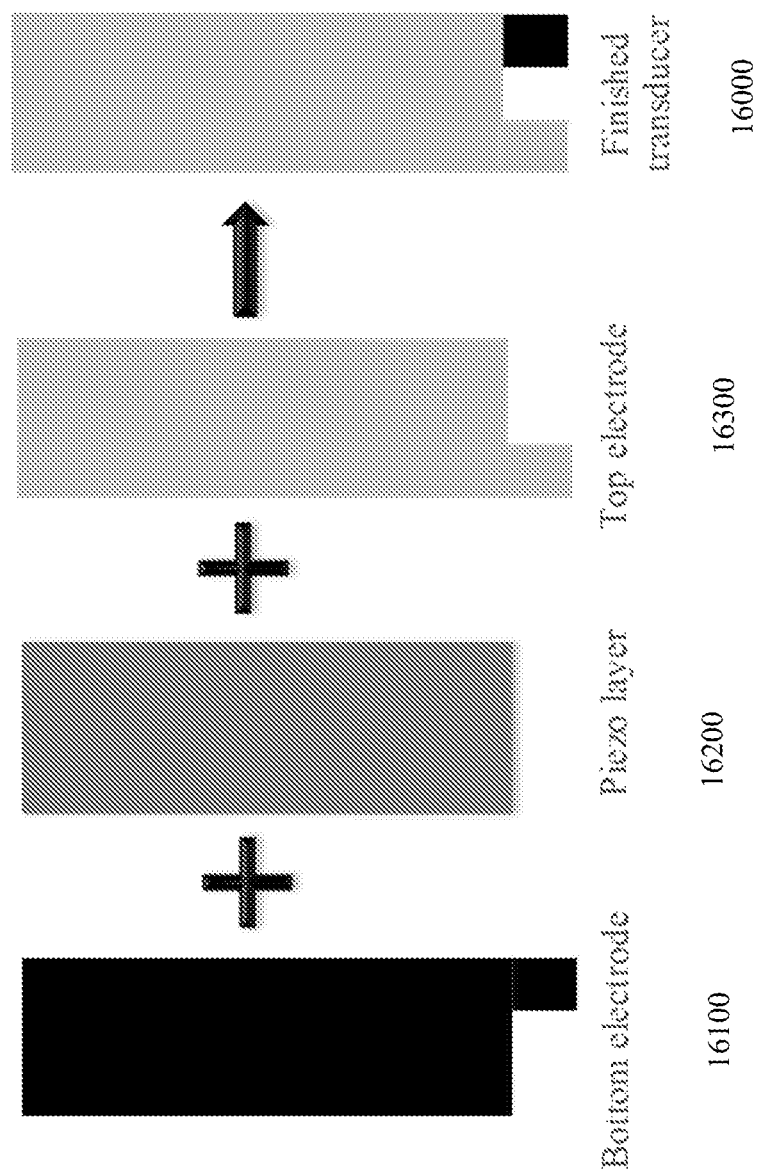
FIG. 16 is a diagram of layers of the poly(3,4-ethylenedioxythiophene) polystyrene sulfonate piezoelectric sensor of FIG. 15 in accordance with certain implementations.

FIG. 15 is a photograph of a poly(3,4-ethylenedioxythiophene) polystyrene sulfonate piezoelectric sensor 15000 which may be used as a pressure transducer to capture and/or measure phonocardiography signals in accordance with certain implementations. The poly(3,4-ethylenedioxythiophene) polystyrene sulfonate piezoelectric sensor 15000 may be implemented on a skin facing side of the vital signs monitoring patch. FIG. 16 is a diagram of layers of the poly(3,4-ethylenedioxythiophene) polystyrene sulfonate piezoelectric sensor 16000 in accordance with certain implementations. The poly(3,4-ethylenedioxythiophene) polystyrene sulfonate piezoelectric sensor 16000 may include a bottom electrode 16100, a piezoelectric layer 16200, and a top electrode 16300, where the piezoelectric layer 16200 is a poly(3,4-ethylenedioxythiophene) polystyrene sulfonate material.

Operationally, the piezoelectric layer 16200 of the poly (3,4-ethylenedioxythiophene) polystyrene sulfonate piezoelectric sensor 16000 may deform in response to response to pressure changes from valvular vibrations, muscular vibrations of myocardium, vascular vibration from sudden distension of arterial walls, vibrations related to acceleration/deceleration of blood flow, and the like, and which are captured as electrical signals via the bottom and top electrodes 16100 and 16300.

Figure 17A:
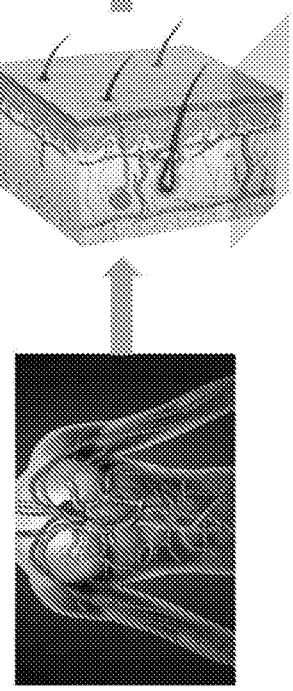
FIGS. 17A-D are an illustration of sound flow mechanics and flow when using a MEMS microphone based phonocardiography sensor in a disposable vital signs monitoring patch in accordance with certain implementations.
Figure 17B:
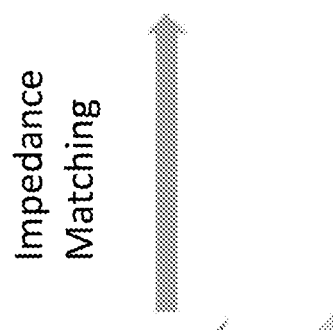
Figure 17C:
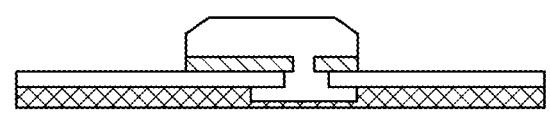
Figure 17D:
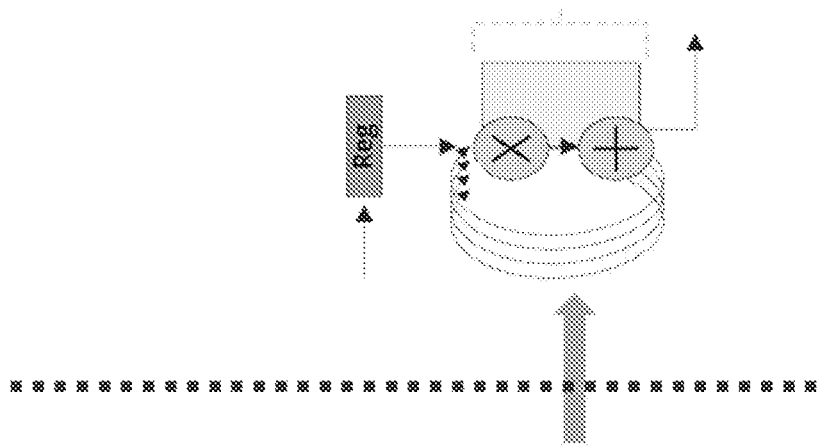
Figure 18:
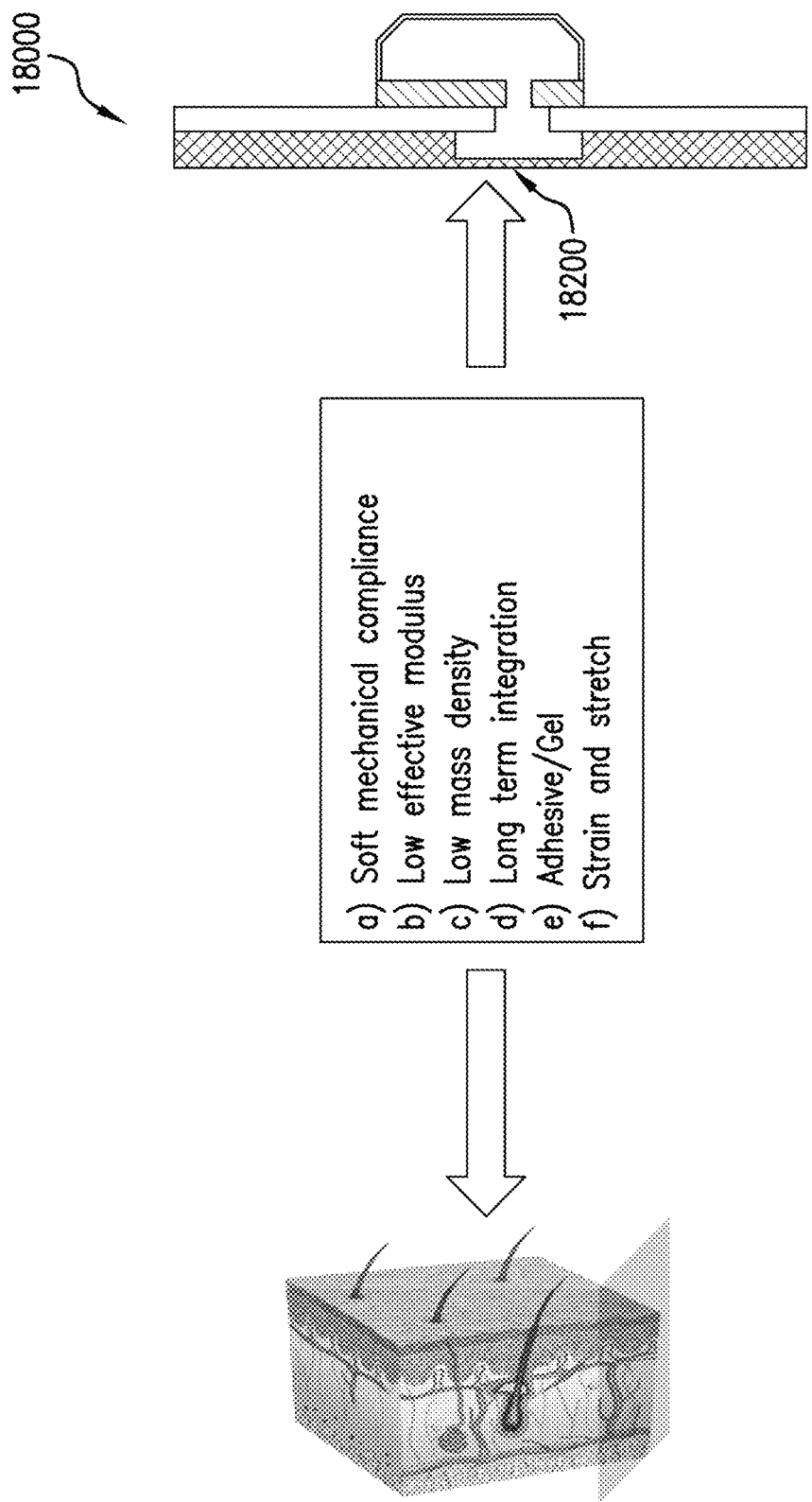
FIG. 18 is an illustration of interface considerations between the MEMS microphone and skin in accordance with certain implementations.

In an implementation, microphones may be used for capturing and/or measuring phonocardiography signals. FIGS. 17A-D and 18 are an illustration of sound flow mechanics and flow considerations when using a MEMS microphone based phonocardiography sensor in accordance with certain implementations. FIG. 17A illustrates a heart, where sound waves emanating from the closing of the heart valves undergo various changes in properties due to absorption, diffraction/scattering, bending, and compression. FIG. 17B illustrates skin, where sound waves emanating from the surface of the skin are further affected by the skin's stiffness, compliance, thickness, absorption (fat content), cellulite density, age, absence or presence of wrinkles, oiliness or dryness, viscoelasticity (Youngs modulus), diffraction/scattering, strain, stretch, and other properties. FIG. 18 illustrates that the interface between skin 18100 and a membrane 18200 located on a disposable vital signs monitoring patch 18000 when implementing a MEMS microphone based phonocardiography sensor require acoustic impedance matching in order to minimize losses. The acoustic impedance matching accounts for or considers soft mechanical compliance, low effective modulus, low mass density, long term integration, adhesive and/or gel being used, and strain and/or stretch characteristics. FIG. 17C illustrates that a MEMS microphone based phonocardiography sensor, which may need to consider mass and mass distribution, mechanical loading (dampening), thickness, modulus/bending stiffness, spring constant, tuning, volume, port dimensions, air seal, sensitivity, and signal-to-noise factors. FIG. 17D illustrates signal processing considerations including for example, active noise cancellation, filtering (signal extraction), synchronization (with ECG signals and other sensor signals), and Frequency Domain (FFT) processing, which may be implemented with techniques usable by one of skill in the art.

Figure 19:
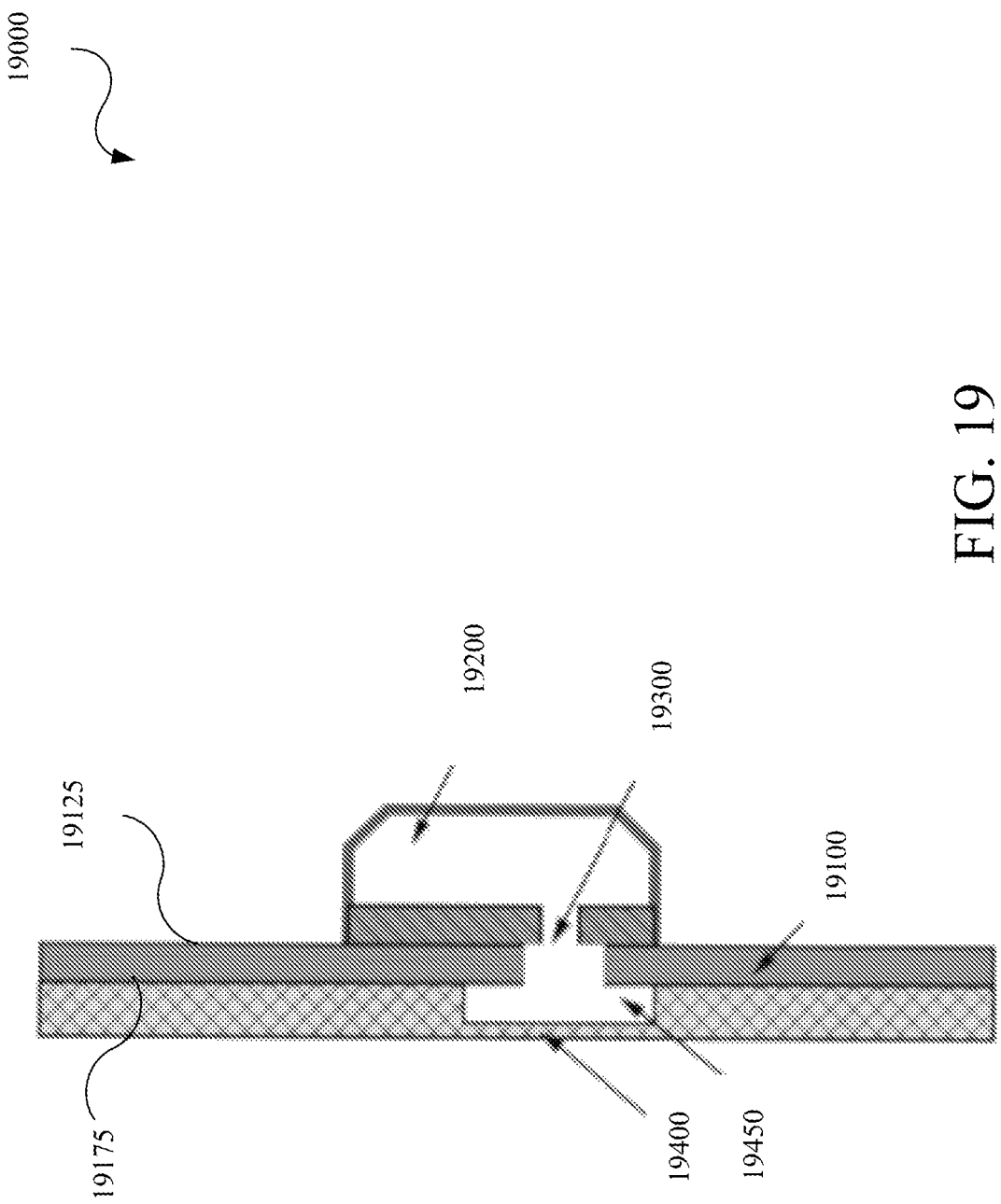
FIG. 19 is an illustration of a MEMS microphone as a phonocardiography sensor in a disposable vital signs monitoring patch in accordance with certain implementations.

FIG. 19 is an illustration of a MEMS microphone based phonocardiography sensor incorporated in a disposable vital signs monitoring patch 19000 in accordance with certain implementations, where the disposable vital signs monitoring patch 19000 includes at least the structure and functionality described herein with respect to FIGS. 1-12. The disposable vital signs monitoring patch 19000 includes a PCBA 19100. A MEMS microphone 19200 may be provided on a non-skin facing surface 19125, where a sound port 19300 may be established in the PCBA 19100 for communication or acoustic communication with a cavity 19450 of a membrane 19400 which may be provided on a skin facing surface 19175. As described herein, sounds originating from closing of heart valves and other heart mechanisms may then emanate from the skin and vibrate against the membrane 19400, amplify through the cavity 19450 and sound port 19300 for capture by the MEMS microphone 19200. The sound waves may then be processed by processors or electronics present on the PCBA 19100 to perform noise cancellation, signal synchronization, digital signal processing, filtering, and the like.

Figure 20A:
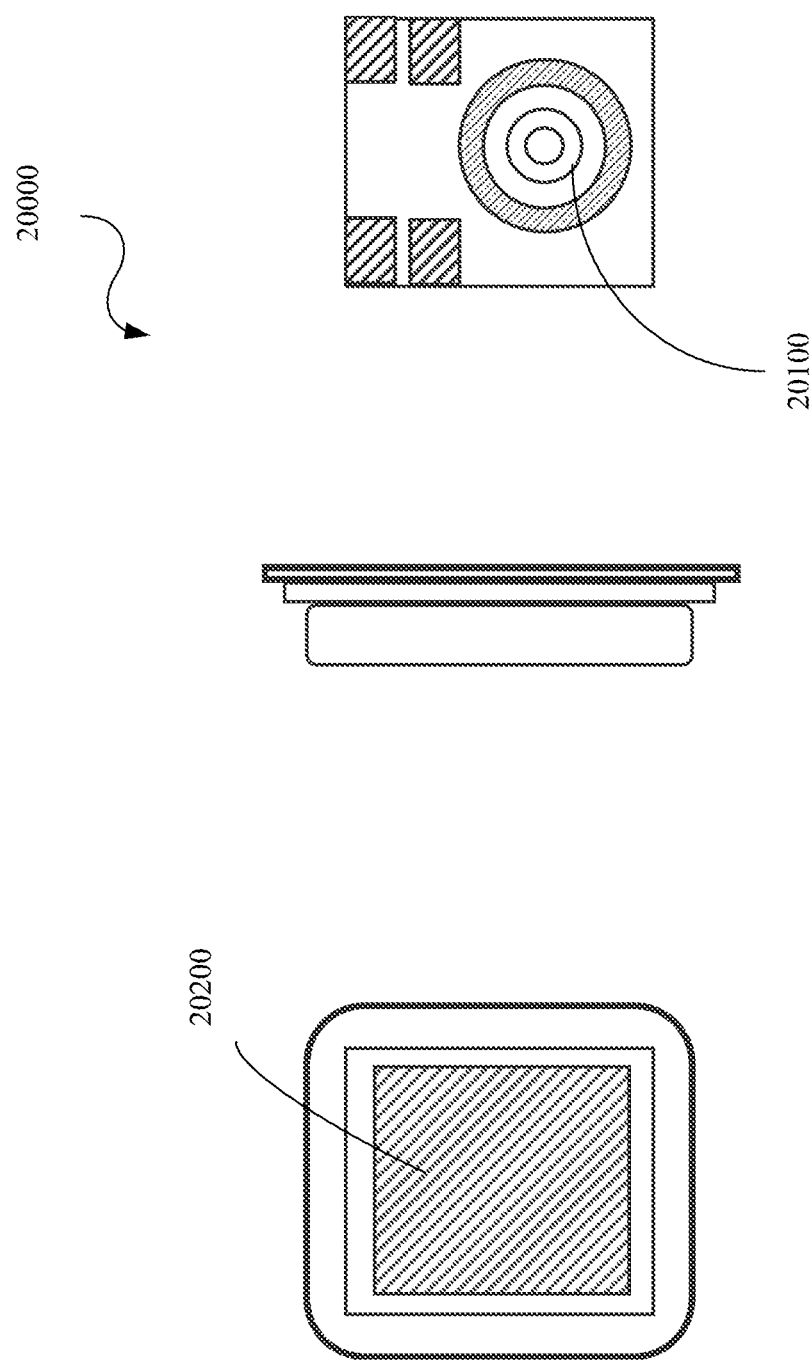
Figure 24A:
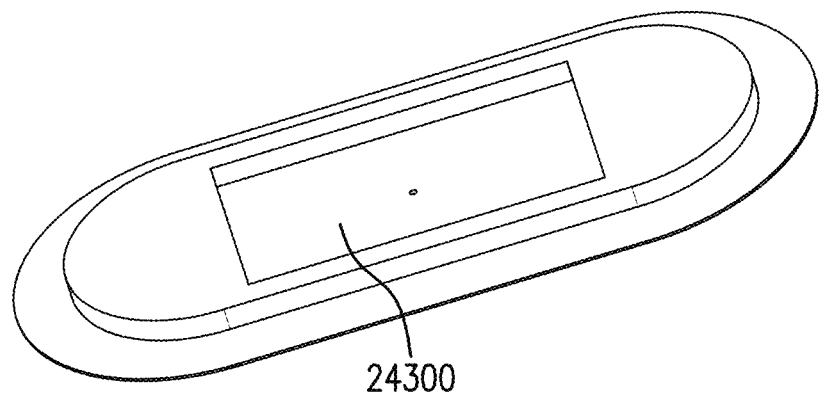
FIGS. 24A-B are diagrams of a disposable vital signs monitoring patch in accordance with certain implementations.
Figure 24B:
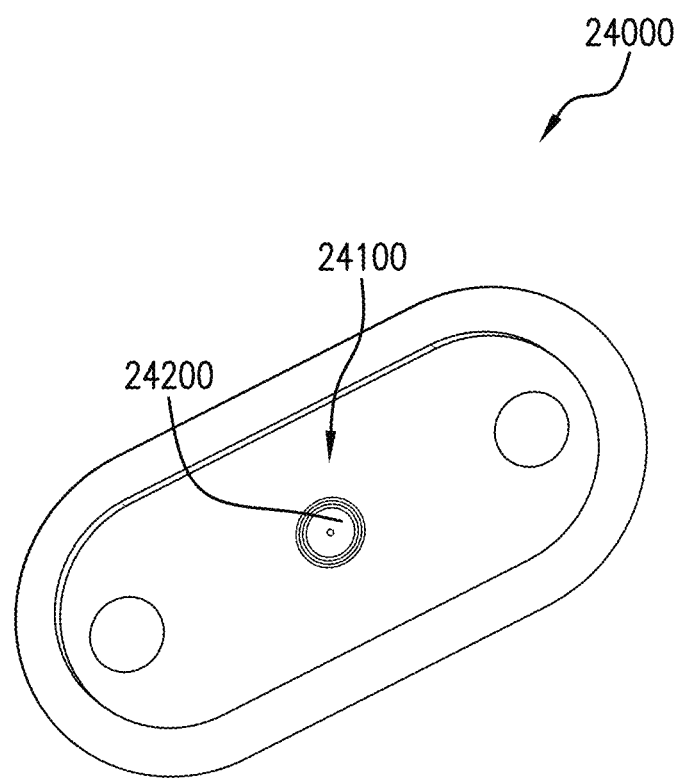

FIGS. 20A-B are illustrations of a MEMS capacitive microphone 20000 as a phonocardiography sensor in a disposable vital signs monitoring patch in accordance with certain implementations. The MEMS capacitive microphone 20000 includes a sound port 20100, a backplate 20200, diaphragm 20300, and application-specific integrated circuit (ASIC) (not shown). The MEMS capacitive microphone 20000 is sized for incorporation into the disposable vital signs monitoring patch as shown in FIGS. 24A and 24B.

Figure 21:
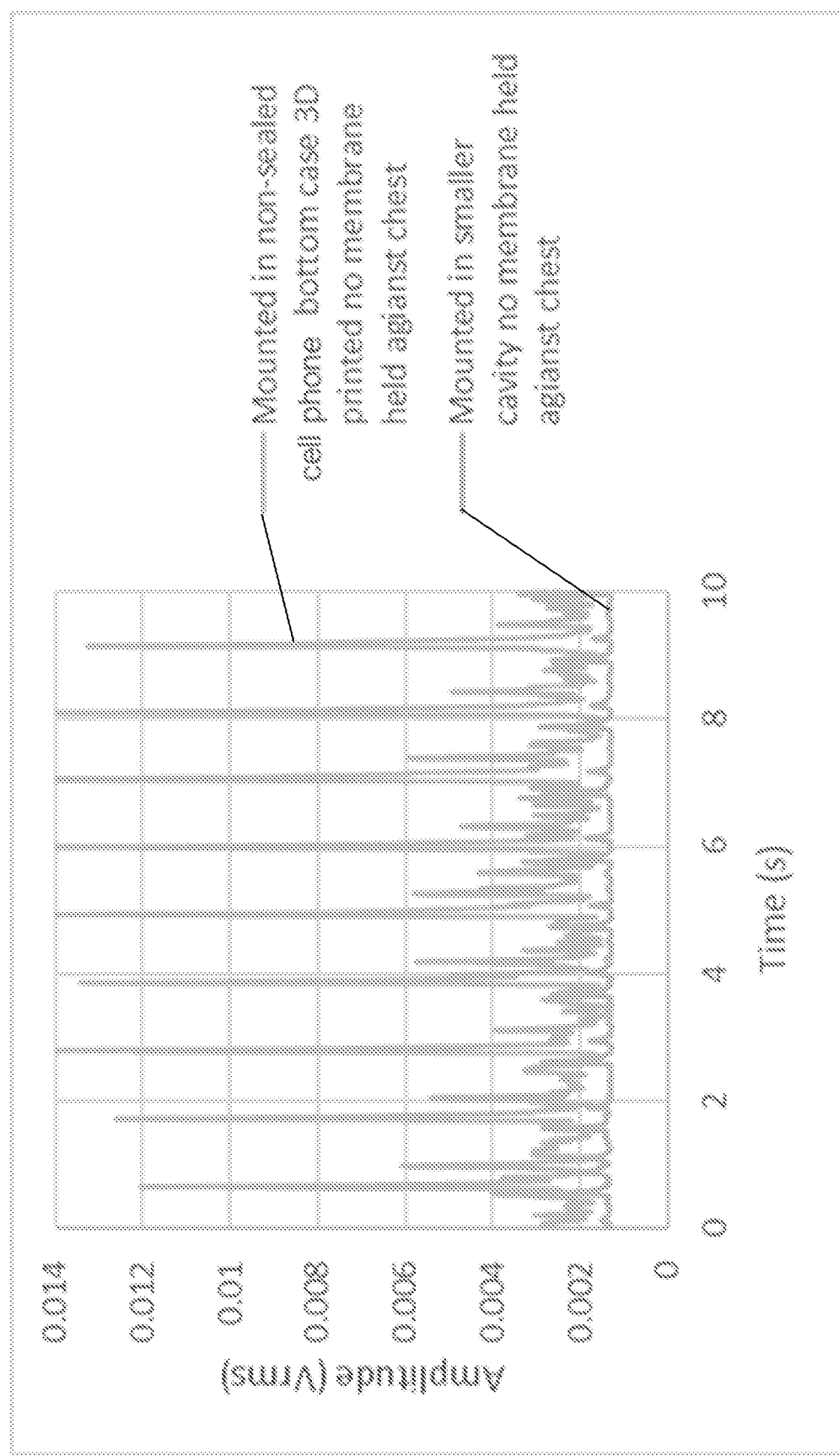
FIG. 21 is a graph of signal differentiation of a MEMS capacitive microphone as a phonocardiography sensor in a disposable vital signs monitoring patch in accordance with certain implementations.

Operationally, as is well-known, a change in air pressure created by sound waves from the heart causes the diaphragm 20300 to flex while the backplate 20200 remains stationary as the air moves through it. The movement of the diaphragm 20300 creates a change in the amount of capacitance between the diaphragm 20300 and the backplate 20200. This is translated into an electrical signal by the ASIC. FIG. 21 illustrates that the incorporation of the MEMS capacitive microphone 20000 into a cavity similar to one available in the disposable vital signs monitoring patch provides sufficient signal differentiation for phonocardiography signal analysis. In particular, FIG. 21 shows comparative data between a cavity size similar to the disposable vital signs monitoring patch and a cellphone cover sized cavity.

Figure 22:
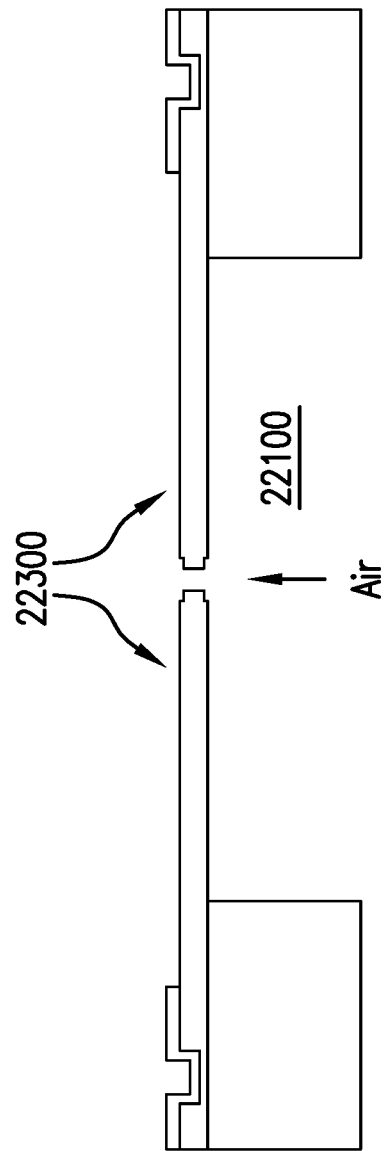
FIG. 22 is an illustration of a MEMS piezoelectric microphone as a phonocardiography sensor in a disposable vital signs monitoring patch in accordance with certain implementations.

FIG. 22 is an illustration of a MEMS piezoelectric microphone 22000 as a phonocardiography sensor in a disposable vital signs monitoring patch in accordance with certain implementations. The MEMS piezoelectric microphone 22000 includes a sound port 22100, piezoelectric plates 22300, and application-specific integrated circuit (ASIC) (not shown). The MEMS piezoelectric microphone 22000 is sized for incorporation into the disposable vital signs monitoring patch as shown in FIGS. 24A and 24B.

Figure 23:
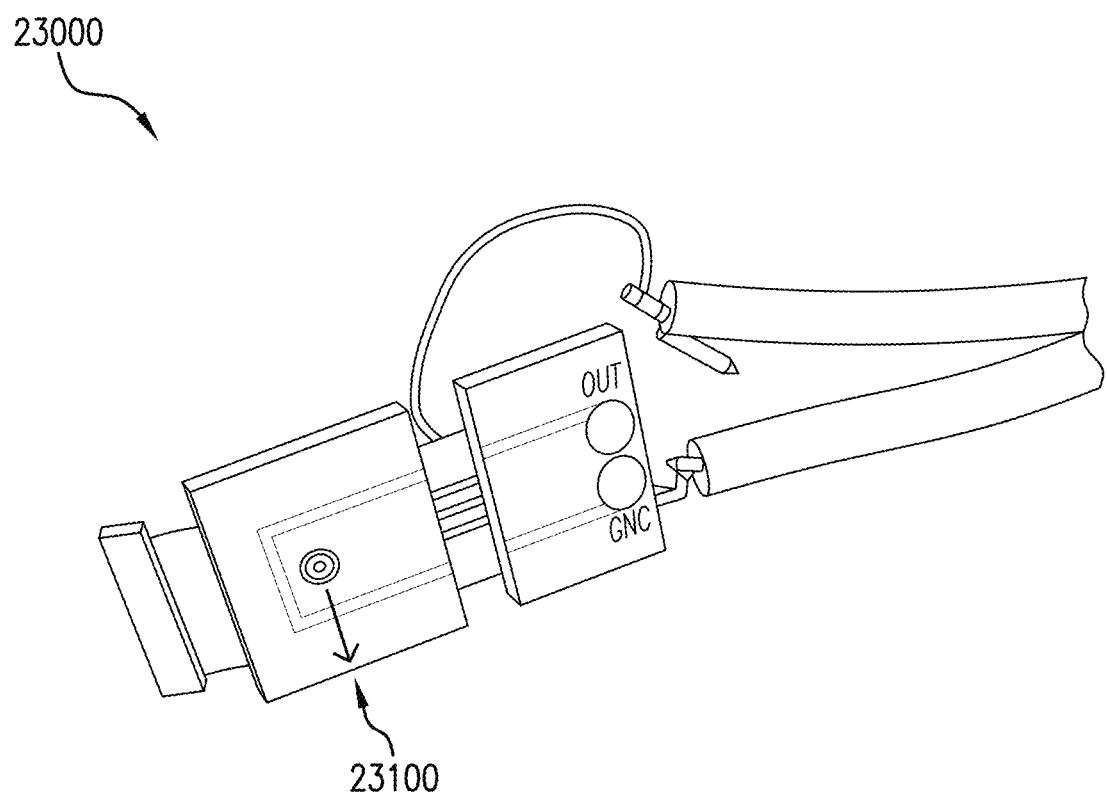
FIG. 23 is a photograph of a MEMS piezoelectric microphone as a phonocardiography sensor in a disposable vital signs monitoring patch in accordance with certain implementations.

Operationally, as is well-known, a change in air pressure created by sound waves from the heart cause the piezoelectric plates 22300 to stress/strain as the air moves through it. The stress/strain on the piezoelectric plates 22300 creates a charge that is translated into an electrical signal by the ASIC. FIG. 23 is a photograph of a MEMS piezoelectric microphone 23000 which shows a bottom port 23100 for placement against a user chest area.

FIGS. 24A-B are diagrams of a disposable vital signs monitoring patch 24000 in accordance with certain implementations. The disposable vital signs monitoring patch 24000 includes the structure and functionality described herein with respect to FIGS. 1A-12 and further includes a phonocardiography sensor 24100 as described with respect to FIGS. 17A-23. FIG. 24A is a top cut-away view of the disposable vital signs monitoring patch 24000 and FIG. 24B is a bottom view of the disposable vital signs monitoring patch 24000, which illustrates an integrated microphone 24100 and in particular, a sound port 24200 and a chamber 24300 extruded underneath the disposable vital signs monitoring patch 24000.

Figure 25B:
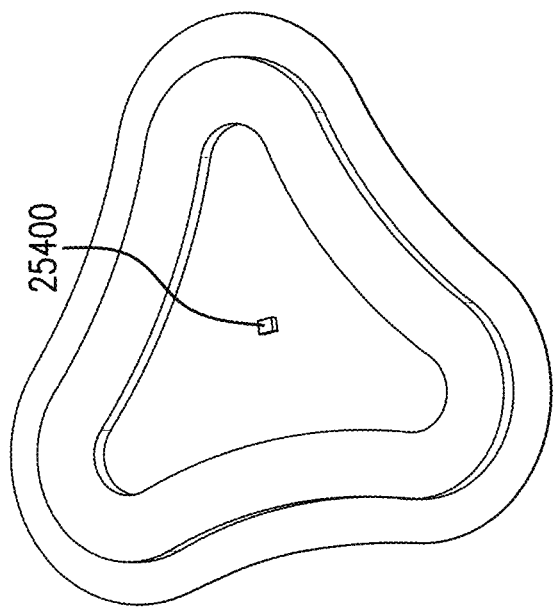
FIGS. 25A-B are diagrams of a disposable vital signs monitoring patch in accordance with certain implementations.
Figure 25A:
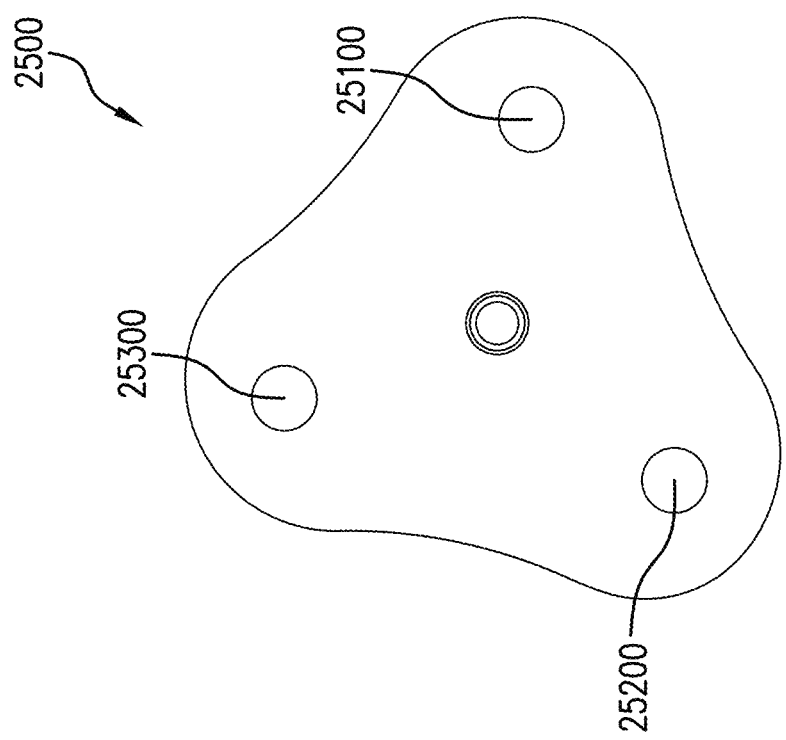
Figure 26:
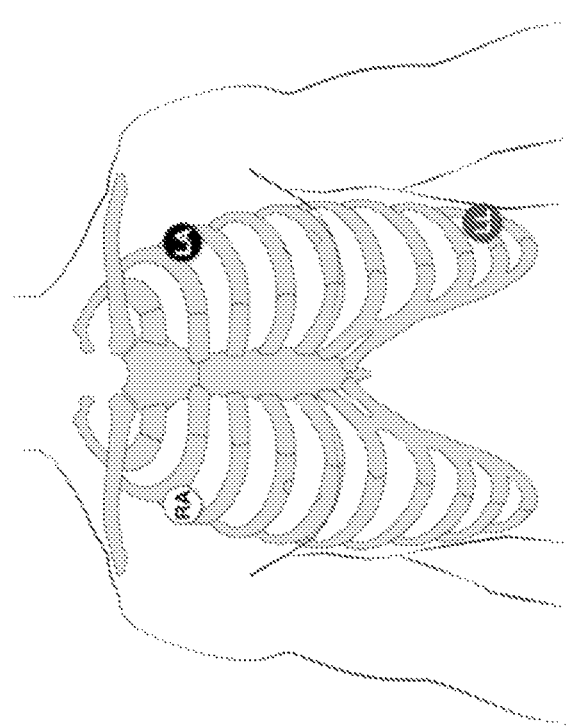
FIG. 26 is a photograph of a placement of the disposable vital signs monitoring patch of FIGS. 25A-B in accordance with certain implementations.

FIGS. 25A-B and FIG. 26 are diagrams of a disposable vital signs monitoring patch 25000 in accordance with certain implementations and electrode placement diagrams in accordance with certain implementations. The disposable vital signs monitoring patch 25000 includes at least the structure and functionality described herein with respect to FIGS. 1A-24. The disposable vital signs monitoring patch 25000 includes electrodes 25100, 25200, and 25300 which approximate a 3-lead ECG system. In addition, the disposable vital signs monitoring patch 25000 may include a sound port 25400 as described herein. In an illustrative example shown in FIG. 26, a first lead is between a Left arm (LA) to a right arm (RA). This is the main implementation shown for the 2-electrode ECG patch described herein. A second lead is between a Left Leg (LL) to the LA and a third lead is between the LL to the RA. In this implementation, the third electrode may be treated as a common sensing element which assists in establishing a driven common electrode circuit by forming a connection with a common amplifier. This enables a differential input amplifier to reject common noise and improves a common mode rejection ratio and ultimately the post-processed ECG signals.

The construction and arrangement of the methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials and components, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps, and decision steps.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A disposable vital signs monitoring patch comprising:
   at least two hydrogel based conductive adhesives configured to contact a user skin surface;
   a medical tape layer having at least a bottom surface, wherein the medical tape layer is configured to bond to the user skin surface, wherein the bottom surface includes at least two printed silver-silver chloride electrodes, and wherein the at least two hydrogel based conductive adhesives are configured to interact between the user skin surface and the at least two printed silver-silver chloride electrodes;
   a double-sided medical tape layer configured to bond to the medical tape layer;
   a printed circuit board assembly (PCBA) layer including at least one vital signs monitoring sensor, a non-chargeable flexible battery, light emitting device (LED), and is connected to the at least two printed silver-silver chloride electrodes, wherein the PCBA is arranged to bond to the double-sided medical tape layer;
   a polyethylene foam layer including a cut-out for the flexible battery and the LED, wherein the PCBA is arranged to bond to the polyethylene foam layer;
   a plunger arranged to operate within a cut-out on the polyethylene foam layer; and
   an acrylic adhesive transfer tape layer having at least a bottom surface, wherein the polyethylene foam layer is arranged to bond to the bottom surface of the acrylic adhesive transfer tape layer,
   wherein the plunger is accessible on the acrylic adhesive transfer tape layer and configured to power on the disposable vital signs monitoring patch via the flexible battery,
   wherein light from the LED is perceivable through the acrylic adhesive transfer tape layer at defined events, and wherein different blinking patterns and time periods indicate power on, power off, wireless device pairing, fall detection, normal operation, and lower power,
   wherein the medical tape layer, the double-sided medical tape layer, the polyethylene foam layer, and the acrylic adhesive transfer tape layer are arranged and configured to provide bonding and sealing against environmental exposure,
   wherein lack of a MAC address on a paired wireless device indicates that the disposable vital signs monitoring patch is off,
   wherein the medical tape layer, the double-sided medical tape layer, the polyethylene foam layer, and the acrylic adhesive transfer tape layer enable strong bonds for a well-sealed and closed device which meets an IPX 67 rating.

2. The patch of claim 1, wherein the PCBA further includes an accelerometer which is configured to detect inclination and fall detection data.

3. The patch of claim 2, wherein the PCBA further includes a wireless component which is configured to transmit at least vital signs data to a vital signs monitoring device.

4. The patch of claim 3, wherein the at least one vital signs monitoring sensor is an electrocardiogram (ECG) sensor.

5. The patch of claim 4, wherein another vital signs monitoring sensor is a phonocardiogram sensor.

6. The patch of claim 5, wherein the accelerometer is configured as a phonocardiogram sensor.

7. The patch of claim 5, wherein the phonocardiogram sensor is a silver-polyvinylidene difluoride (Ag-PVDF) piezoelectric sensor.

8. The patch of claim 7, wherein the polyvinylidene difluoride (PVDF) piezoelectric sensor includes an Ag-PVDF sensor strip and a pair of electrodes, wherein the Ag-PVDF strip is configured to stretch in a defined direction in response to heart related activity and the pair of electrodes is configured to capture electrical signals corresponding to the stretching of the Ag-PVDF strip.

9. The patch of claim 8, wherein the Ag-PVDF sensor strip includes multiple layers including at least a mylar layer, coating layers, upper and lower shield layers, film layers, upper and lower silver ink layers, and an adhesive transfer tape layer.

10. The patch of claim 5, wherein the phonocardiogram sensor is a poly(3,4-ethylenedioxythiophene) polystyrene sulfonate piezoelectric sensor.

11. The patch of claim 10, wherein the poly(3,4-ethylenedioxythiophene) polystyrene sulfonate piezoelectric sensor includes a bottom electrode, a piezoelectric layer of poly(3,4-ethylenedioxythiophene) polystyrene sulfonate material, and a top electrode, wherein the piezoelectric layer is configured to deform in response to heart related activity and the bottom and top electrodes are configured to capture electrical signals corresponding to the deformation of the piezoelectric layer.

12. The patch of claim 5, wherein the phonocardiogram sensor is a MEMS piezoelectric microphone.

13. The patch of claim 12, wherein the MEMS piezoelectric microphone includes a membrane having a cavity in acoustic communication with a sound port established on the PCBA.

14. The patch of claim 4, wherein the at least two printed silver-silver chloride electrodes is at least three silver-silver chloride electrodes, wherein a third electrode is a common sensing element which is connected to a common amplifier and enables a differential input amplifier to reject common noise present in ECG sensor signals, wherein the common amplifier and the differential input amplifier are on the PCBA.

15. A disposable vital signs monitoring device comprising:
   at least two hydrogel based conductive adhesives configured to contact a user skin surface;
   a medical adhesive layer having at least a bottom surface, wherein the medical adhesive layer is configured to bond to the user skin surface, wherein the bottom surface includes at least two printed silver-silver chloride electrodes, and wherein the at least two hydrogel based conductive adhesives are configured to interact between the user skin surface and the at least two printed silver-silver chloride electrodes;
   a double-sided medical adhesive layer configured to bond to the medical adhesive layer;
   a printed circuit board assembly (PCBA) layer including an electrocardiogram (ECG) sensor, a non-rechargeable battery, light emitting device (LED), wherein the PCBA is configured to connect to the at least two printed silver-silver chloride electrodes and the PCBA is arranged to bond to the double-sided medical adhesive layer;
   a foam layer including a cut-out for the flexible battery and the LED, wherein the PCBA is arranged to bond to the foam layer;
   a plunger arranged to operate within a cut-out on the foam layer; and
   an acrylic adhesive transfer tape layer having at least a bottom surface, wherein the foam layer is arranged to bond to the bottom surface of the acrylic adhesive transfer tape layer,
   wherein the plunger is user operable on the acrylic adhesive transfer tape layer and configured to power on the disposable vital signs monitoring patch via the flexible battery,
   wherein light from the LED is perceivable through the acrylic adhesive transfer tape layer at defined sequences and intervals for different events to indicate power on, power off, wireless device pairing, fall detection, normal operation, and low power,
   wherein lack of a MAC address on a paired wireless device indicates that the disposable vital signs monitoring patch is off, and
   wherein the medical adhesive layer, the double-sided medical adhesive layer, the foam layer, and the acrylic adhesive transfer tape layer are arranged and configured to provide bonding and sealing against environmental exposure which meets an IPX 67 rating.

* * * * *